(12) United States Patent
Ma

(10) Patent No.: US 9,447,113 B2
(45) Date of Patent: Sep. 20, 2016

(54) ORGANIC ELECTROLUMINESCENT MATERIALS AND DEVICES

(71) Applicant: UNIVERSAL DISPLAY CORPORATION, Ewing, NJ (US)

(72) Inventor: Bin Ma, Plainsboro, NJ (US)

(73) Assignee: UNIVERSAL DISPLAY CORPORATION, Ewing, NJ (US)

(*) Notice: Subject to any disclaimer, the term of this patent is extended or adjusted under 35 U.S.C. 154(b) by 0 days.

(21) Appl. No.: 14/601,963

(22) Filed: Jan. 21, 2015

(65) Prior Publication Data
US 2015/0171345 A1    Jun. 18, 2015

Related U.S. Application Data

(63) Continuation of application No. 13/347,305, filed on Jan. 10, 2012, now Pat. No. 8,969,592.

(51) Int. Cl.
| C07D 495/04 | (2006.01) |
| C07D 495/14 | (2006.01) |
| H01L 51/00  | (2006.01) |
| H01L 51/50  | (2006.01) |
| C07F 7/08   | (2006.01) |

(52) U.S. Cl.
CPC ........... *C07D 495/04* (2013.01); *C07D 495/14* (2013.01); *C07F 7/0812* (2013.01); *H01L 51/0054* (2013.01); *H01L 51/0071* (2013.01); *H01L 51/0072* (2013.01); *H01L 51/0074* (2013.01); *H01L 51/0094* (2013.01); *H01L 51/0085* (2013.01); *H01L 51/5012* (2013.01); *H01L 51/5016* (2013.01); *H01L 51/5096* (2013.01)

(58) Field of Classification Search
CPC ........................ C07D 495/04; C07D 495/14
See application file for complete search history.

(56) References Cited

U.S. PATENT DOCUMENTS

| | | | |
|---|---|---|---|
| 3,278,552 A  | 10/1966 | Geering |
| 4,769,292 A  | 9/1988  | Tang et al. |
| 5,061,569 A  | 10/1991 | VanSlyke et al. |
| 5,247,190 A  | 9/1993  | Friend et al. |
| 5,703,436 A  | 12/1997 | Forrest et al. |
| 5,707,745 A  | 1/1998  | Forrest et al. |
| 5,834,893 A  | 11/1998 | Bulovic et al. |
| 5,844,363 A  | 12/1998 | Gu et al. |
| 6,013,982 A  | 1/2000  | Thompson et al. |
| 6,087,196 A  | 7/2000  | Sturm et al. |
| 6,091,195 A  | 7/2000  | Forrest et al. |
| 6,097,147 A  | 8/2000  | Baldo et al. |
| 6,294,398 B1 | 9/2001  | Kim et al. |
| 6,303,238 B1 | 10/2001 | Thompson et al. |
| 6,337,102 B1 | 1/2002  | Forrest et al. |
| 6,468,819 B1 | 10/2002 | Kim et al. |
| 6,528,187 B1 | 3/2003  | Okada |
| 6,687,266 B1 | 2/2004  | Ma et al. |
| 6,835,469 B2 | 12/2004 | Kwong et al. |
| 6,921,915 B2 | 7/2005  | Takiguchi et al. |
| 7,087,321 B2 | 8/2006  | Kwong et al. |
| 7,090,928 B2 | 8/2006  | Thompson et al. |
| 7,154,114 B2 | 12/2006 | Brooks et al. |
| 7,250,226 B2 | 7/2007  | Tokito et al. |
| 7,279,704 B2 | 10/2007 | Walters et al. |
| 7,332,232 B2 | 2/2008  | Ma et al. |
| 7,338,722 B2 | 3/2008  | Thompson et al. |
| 7,393,599 B2 | 7/2008  | Thompson et al. |
| 7,396,598 B2 | 7/2008  | Takeuchi et al. |
| 7,431,968 B1 | 10/2008 | Shtein et al. |
| 7,445,855 B2 | 11/2008 | Mackenzie et al. |
| 7,534,505 B2 | 5/2009  | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0151042 A1 | 8/2003 | Marks et al. |
| 2003/0152802 A1 | 8/2003 | Tsuboyama et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2004/0249156 A1* | 12/2004 | Kim .................... C07F 15/0033 546/2 |
| 2005/0025993 A1 | 2/2005 | Thompson et al. |
| 2005/0112407 A1 | 5/2005 | Ogasawara et al. |
| 2005/0238919 A1 | 10/2005 | Ogasawara |

(Continued)

FOREIGN PATENT DOCUMENTS

| EP | 0650955 | 5/1995 |
| EP | 1725079 | 11/2006 |

(Continued)

OTHER PUBLICATIONS

Izawa et al. "Molecular modification of 2,7-diphenyl[1]benzothieno[3,2-b]benzothiophene (DPh-BTBT) with diarylamino substituents: from crystalline order to amorphous state in evaporated thin films" Chemical Letters, 2009, vol. 38, pp. 420-421.*

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

(Continued)

*Primary Examiner* — Joseph Kosack
(74) *Attorney, Agent, or Firm* — Duane Morris LLP

(57) ABSTRACT

Novel heterocyclic materials are disclosed. The materials contain a fused tetracyclic structure that can improve the properties of OLED devices when the novel heterocyclic materials are incorporated into such devices.

20 Claims, 3 Drawing Sheets

(56) References Cited

U.S. PATENT DOCUMENTS

| | | |
|---|---|---|
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2013/0207047 A1 | 8/2013 | Suda et al. |

FOREIGN PATENT DOCUMENTS

| | | | |
|---|---|---|---|
| EP | 2034538 | | 3/2009 |
| JP | 200511610 | | 1/2005 |
| JP | 2007123392 | | 5/2007 |
| JP | 2007254297 | | 10/2007 |
| JP | 2008074939 | | 4/2008 |
| JP | 2009246139 | A * | 10/2009 |
| WO | 0139234 | | 5/2001 |
| WO | 0202714 | | 1/2002 |
| WO | 0215645 | | 2/2002 |
| WO | 03040257 | | 5/2003 |
| WO | 03060956 | | 7/2003 |
| WO | 2004093207 | | 10/2004 |
| WO | 2004107822 | | 12/2004 |
| WO | 2005014551 | | 2/2005 |
| WO | 2005019373 | | 3/2005 |
| WO | 2005030900 | | 4/2005 |
| WO | 2005089025 | | 9/2005 |
| WO | 2005123873 | | 12/2005 |
| WO | 2006009024 | | 1/2006 |
| WO | 2006056418 | | 6/2006 |
| WO | 2006072002 | | 7/2006 |
| WO | 2006082742 | | 8/2006 |
| WO | 2006098120 | | 9/2006 |
| WO | 2006100298 | | 9/2006 |
| WO | 2006103874 | | 10/2006 |
| WO | 2006114966 | | 11/2006 |
| WO | 2006132173 | | 12/2006 |
| WO | 2007002683 | | 1/2007 |
| WO | 2007004380 | | 1/2007 |
| WO | 2007063754 | | 6/2007 |
| WO | 2007063796 | | 6/2007 |
| WO | 2008056746 | | 5/2008 |
| WO | 2008101842 | | 8/2008 |
| WO | 2008132085 | | 11/2008 |
| WO | 2009000673 | | 12/2008 |
| WO | 2009003898 | | 1/2009 |
| WO | 2009008311 | | 1/2009 |
| WO | 2009018009 | | 2/2009 |
| WO | 2009050290 | | 4/2009 |
| WO | 2009021126 | | 5/2009 |
| WO | 2009062578 | | 5/2009 |
| WO | 2009063833 | | 5/2009 |
| WO | 2009066778 | | 5/2009 |
| WO | 2009066779 | | 5/2009 |
| WO | 2009086028 | | 7/2009 |
| WO | 2009100991 | | 8/2009 |

OTHER PUBLICATIONS

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato)beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

(56) References Cited

OTHER PUBLICATIONS

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl, Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am, Chem. Soc., 122(8):1832-1833 (2000).

Salbeck, J. et al., "Low Molecular Organic Glasses for Blue Electroluminescence," Synthetic Metals, 91209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Patai, et al., "Synthesis of benzoselenopheno[2,3-b]enzoselenophenes from 1, 1-diarylethylenes and selenium oxychloride," Journal of the Chemical Society, 1962, pp. 734.739.
Banihashemi et al. (CAS Accession No. 1999:2496).
Banihashemi et al. (CAS Accession No. 2000:447136).
Moustafa et al. (CAS Accession No. 2003:524817).

* cited by examiner

Formula I

ORGANIC ELECTROLUMINESCENT MATERIALS AND DEVICES

CROSS-REFERENCE TO RELATED APPLICATIONS

This application is a divisional application of U.S. patent application Ser. No. 13/347,305, filed Jan. 10, 2012, the entire content of which is incorporated herein by reference.

PARTIES TO A JOINT RESEARCH AGREEMENT

The claimed invention was made by, on behalf of, and/or in connection with one or more of the following parties to a joint university corporation research agreement: The Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to novel heterocyclic host materials suitable for incorporation into OLED devices. Devices incorporating the novel host materials described herein are expected to have improved properties such as increased efficiency and stability.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

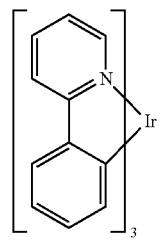

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect a compound having the formula:

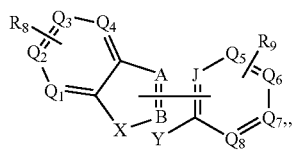

Formula I is provided. In the compound of Formula I, $Q_1$ to $Q_8$ are independently selected from CH and N, and wherein $Q_1$ to $Q_8$ may be further substituted. A is directly bonded to J and B is directly bonded to Y, or wherein A is directly bonded to Y and B is directly bonded to J. A, B, and J are carbon atoms. X and Y are independently selected from the group consisting of O, S, and Se. $R_8$ and $R_9$ independently represent mono, di, tri, tetra substitution, or no substitution. $R_8$ and $R_9$ are independently selected from the group consisting of deuterium, alkyl, cycloalkyl, arylalkyl, amino, silyl, germyl, alkenyl, cycloalkenyl, heteroalkenyl, alkynyl, aryl, heteroaryl, and combinations thereof, and at least one of $R_8$ and $R_9$ is not hydrogen or deuterium.

In one aspect, at least one of $R_8$ and $R_9$ is independently selected from the group consisting of:

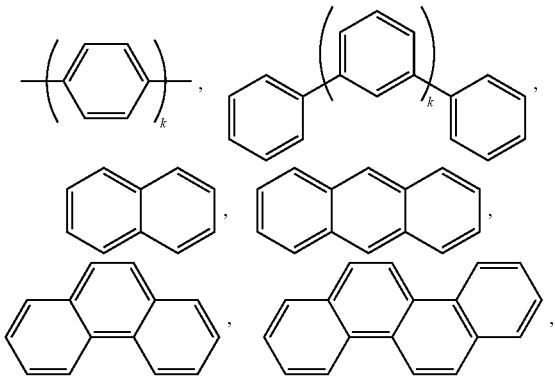

-continued

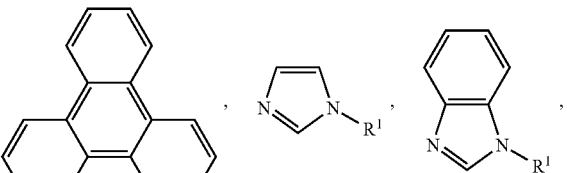

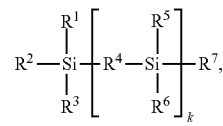

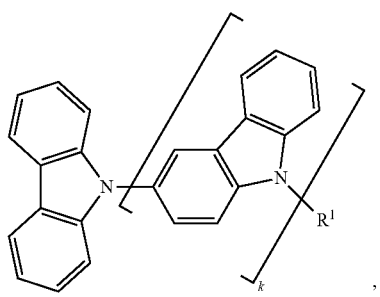

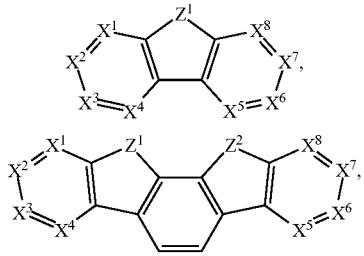

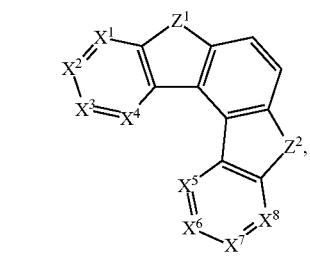

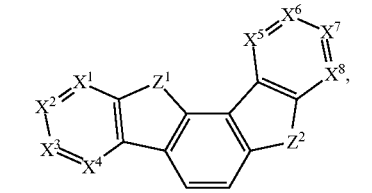

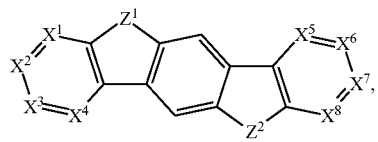

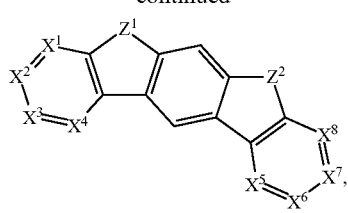

wherein $R^1$ to $R^7$ is independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof k is an integer from 0 to 20, $X^1$ to $X^8$ are independently selected from C, CH, and N, $Z^1$ and $Z^2$ is selected from $NR^1$, O, or S; and $R_8$ and $R_9$ may be further substituted.

In one aspect, the compound has the formula:

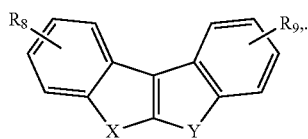

Formula II

In one aspect, the compound has the formula:

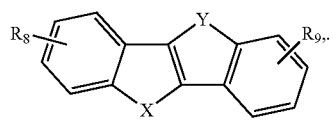

Formula III

In one aspect, one of $Q_1$ to $Q_8$ is N.

In one aspect, at least one of $R_8$ and $R_9$ has the formula:

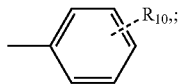

Formula IV wherein $R_{10}$ represents mono, di, tri, tetra substitution, or no substitution and wherein $R_{10}$ is selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

In one aspect, $R_{10}$ represents mono-substitution and is selected from the group consisting of:

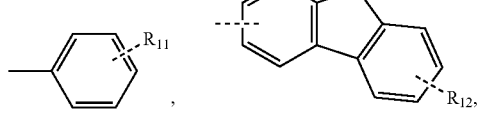

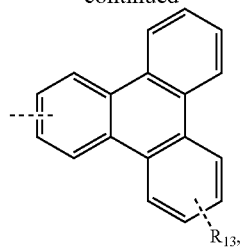

SiRR'R" and combinations thereof. Z is selected from the group consisting of NR, S, O, and Se. $R_{11}$, $R_{12}$, and $R_{13}$ represents mono, di, tri, tetra substitution, or no substitution. R, R', R", $R_{11}$, $R_{12}$, and $R_{13}$ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

In one aspect, at least one of $R_8$ and $R_9$ is independently selected from the group consisting of:

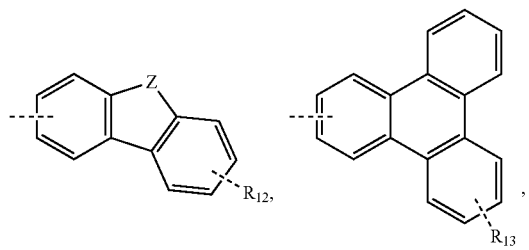

SiRR'R" and combinations thereof. Z is selected from the group consisting of NR, S, O, and Se. $R_{12}$ and $R_{13}$ represents mono, di, tri, tetra substitution, or no substitution, and R, R', R", $R_{12}$, and $R_{13}$ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

In one aspect, X and Y are S.

In one aspect, at least one of $R_8$ and $R_9$ is

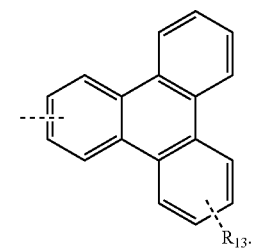

In one aspect, at least one of $R_8$ and $R_9$ is

In one aspect, at least one of $R_8$ and $R_9$ is SiRR'R". In another aspect, $R_8$ is ortho or para to X, and wherein $R_9$ is ortho or para to Y. In one aspect, $R_8$ is ortho or para to X, and wherein $R_9$ is ortho or para to Y. In one aspect, $R_8$ is hydrogen or deuterium.

In one aspect, the compound is selected from the group consisting of Compound 1-Compound 52.

In one aspect, a first device comprising an organic light emitting device, further comprising an anode, a cathode, and an organic layer, disposed between the anode and the cathode, comprising a compound having the formula:

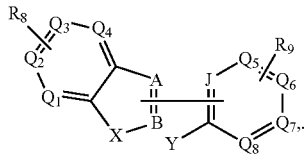

Formula I

In the compound of Formula I, $Q_1$ to $Q_8$ are independently selected from CH and N, and wherein $Q_1$ to $Q_8$ may be further substituted. A is directly bonded to J and B is directly bonded to Y, or wherein A is directly bonded to Y and B is directly bonded to J. A, B, and J are carbon atoms. X and Y are independently selected from the group consisting of O, S, and Se. $R_8$ and $R_9$ independently represent mono, di, tri, tetra substitution, or no substitution. $R_8$ and $R_9$ are independently selected from the group consisting of deuterium, alkyl, cycloalkyl, arylalkyl, amino, silyl, germyl, alkenyl, cycloalkenyl, heteroalkenyl, alkynyl, aryl, heteroaryl, and combinations thereof, and at least one of $R_8$ and $R_9$ is not hydrogen or deuterium.

In one aspect, the organic layer is an emissive layer and the compound of Formula I is a host. In one aspect, the organic layer further comprises an emissive dopant.

In one aspect, the emissive dopant is a transition metal complex having at least one ligand or part of the ligand if the ligand is more than bidentate selected from the group consisting of:

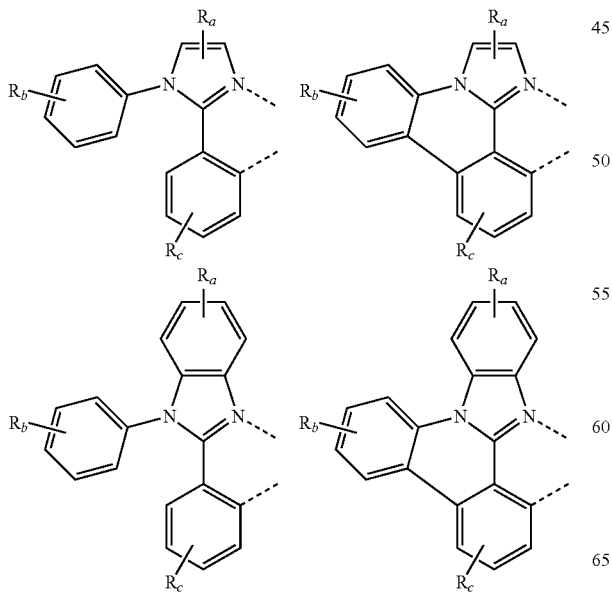

-continued

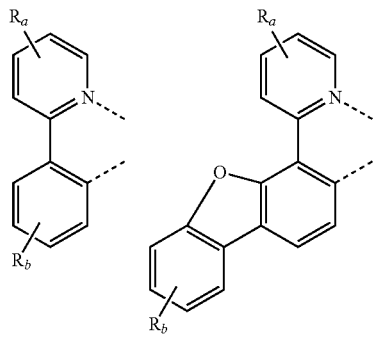

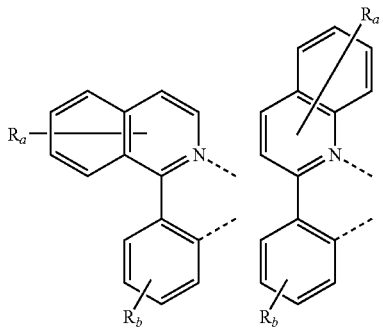

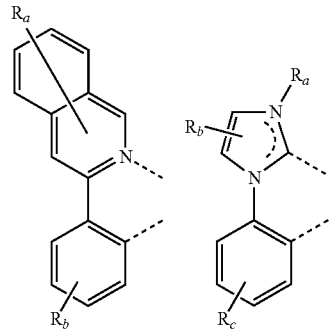

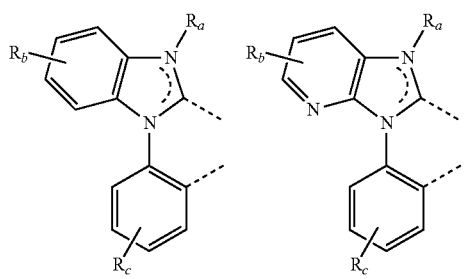

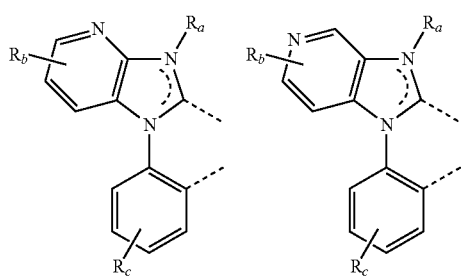

-continued

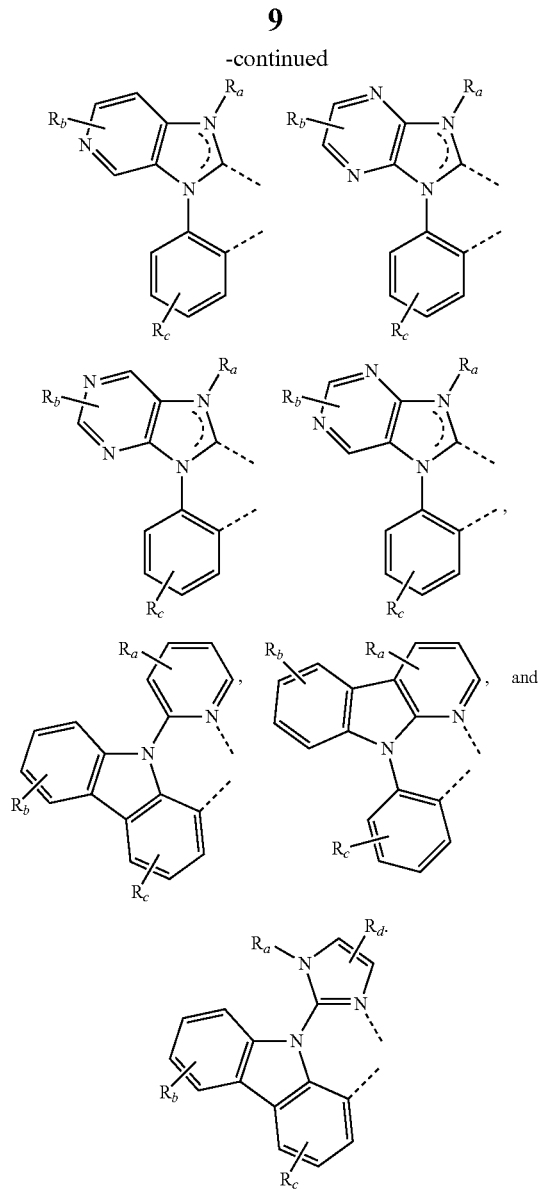

R$_a$, R$_b$, and R$_c$ may represent mono, di, tri or tetra substitutions, or no substitution, and R$_a$, R$_b$, and R$_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of R$_a$, R$_b$, and R$_c$ are optionally joined to form a fused ring or form a multidentate ligand.

In one aspect, the device further comprises a second organic layer that is a non-emissive layer and the compound having Formula I is a material in the second organic layer.

In one aspect, the second organic layer is a blocking layer and the compound having Formula I is a blocking material in the second organic layer.

In one aspect, the first device is a consumer product. In one aspect, the first device is an organic light-emitting device. In one aspect, the first device comprises a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
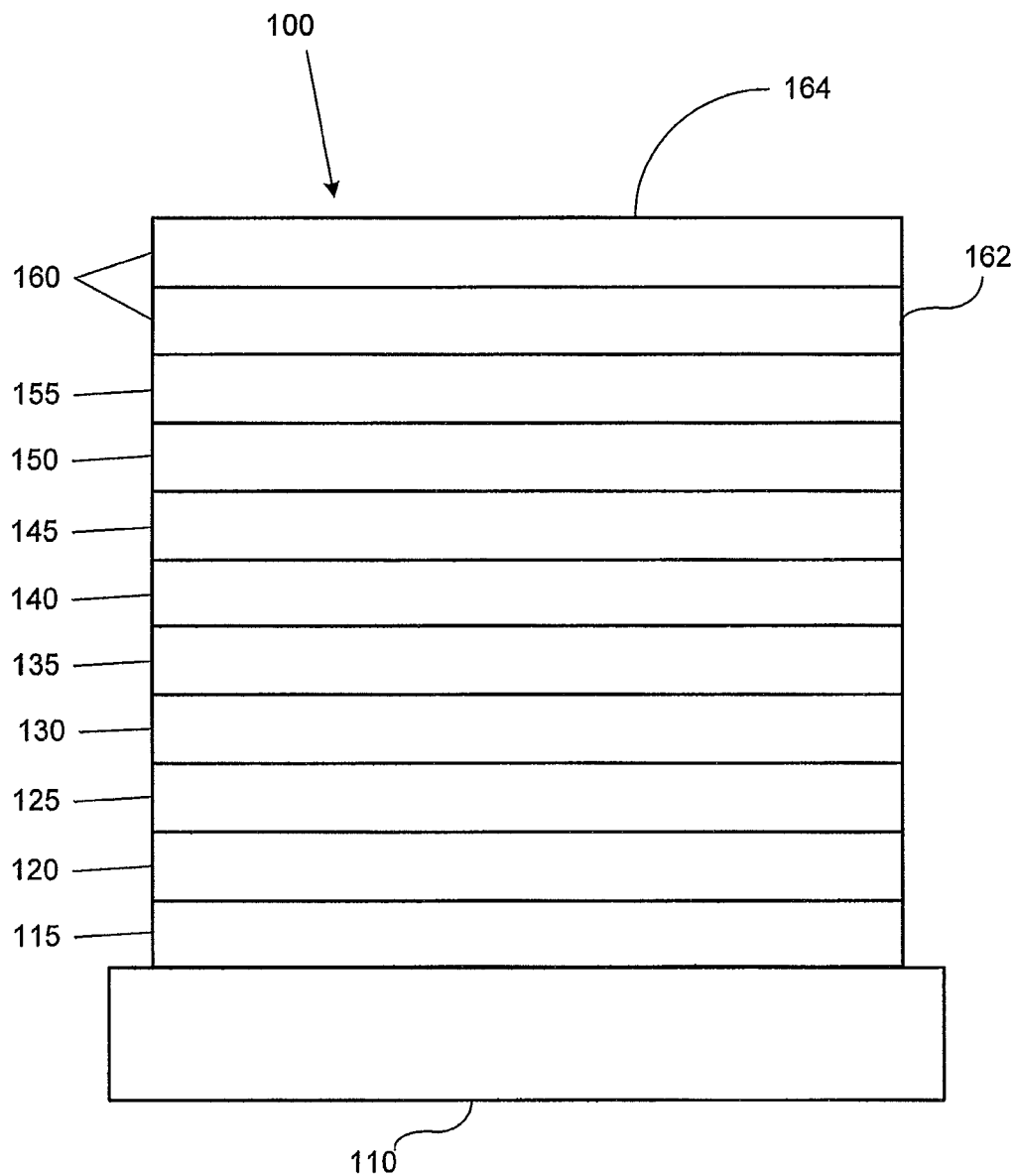
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
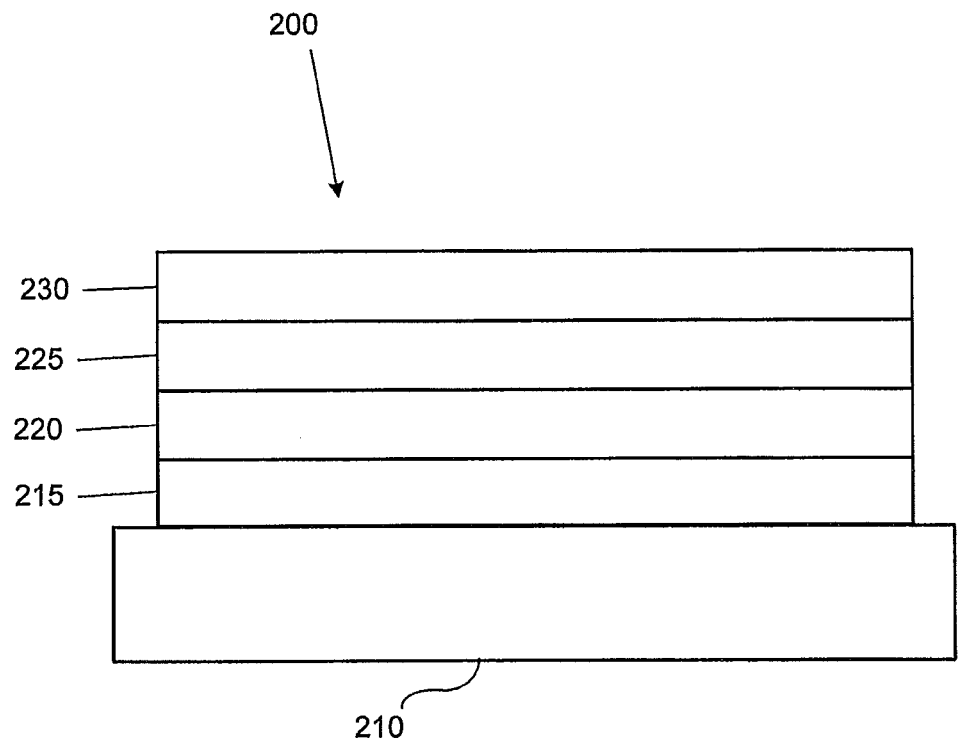
FIG. 2 shows an inverted organic light emitting device that does not have a separate electron transport layer.
Figure 3:
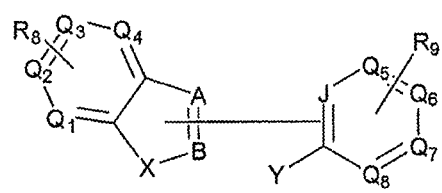
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment a compound having the formula:

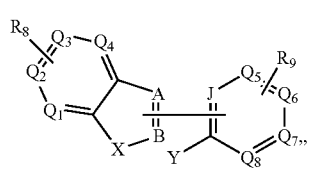

Formula I is provided. In the compound of Formula I, $Q_1$ to $Q_8$ are independently selected from CH and N, and wherein $Q_1$ to $Q_8$ may be further substituted. A is directly bonded to J and B is directly bonded to Y, or wherein A is directly bonded to Y and B is directly bonded to J. A, B, and J are carbon atoms. X and Y are independently selected from the group consisting of O, S, and Se. $R_8$ and $R_9$ independently represent mono, di, tri, tetra substitution, or no substitution. $R_8$ and $R_9$ are independently selected from the group consisting of deuterium, alkyl, cycloalkyl, arylalkyl, amino, silyl, germyl, alkenyl, cycloalkenyl, heteroalkenyl, alkynyl, aryl, heteroaryl, and combinations thereof, and at least one of $R_8$ and $R_9$ is not hydrogen or deuterium.

DBT (dibenzothiophene) containing hosts show significant device performance improvement with respect to device stability and efficiency when such compounds are incorporated into\phosphorescent OLED devices, see, e.g. WO 2009021126. Compounds of Formula I have an additional ring fused into the ring system, making them tetracyclic compounds, whereas DBT and DBF (dibenzofuran) are tricyclic ring systems. However, based on DFT calculations, the triplet energy of molecules containing the core structure of compounds of Formula I show relatively high energy, especially when X and Y are heteroatoms and on the same side, i.e. Compounds of Formula II. Molecules containing the core in compounds of Formula II have higher calculated triplet energy than molecules containing the core of compounds of Formula III. These results are summarized in Table 1.

TABLE 1

Calculated Energy Levels foe Molecules Containing the Core of Compounds of Formula I[a]

| Molecule # | Structure | HOMO (ev) | LUMO (ev) | HOMO – LUMO (ev) | Dipole (Debye) | Calc. T1 (nm) |
|---|---|---|---|---|---|---|
| 1. | 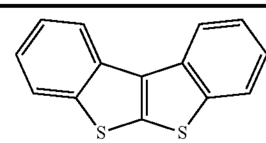 | −5.60 | −0.86 | −4.74 | 1.30 | 418 |
| 2. | 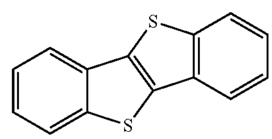 [SMILES: c1ccc2c(c1)sc1c3ccccc3sc21] | −5.58 | −1.26 | −4.32 | 0.00 | 462 |
| 3. | 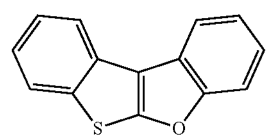 [SMILES: c1ccc2c(c1)oc1sc3ccccc3c12] | −5.57 | −0.61 | −4.96 | 1.19 | 394 |
| 4. | 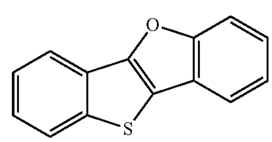 [SMILES: c1ccc2c(c1)oc1c3ccccc3sc21] | −5.55 | −1.17 | −4.38 | 0.24 | 456 |
| 5. | 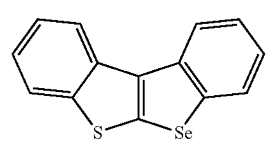 [SMILES: c1ccc2c(c1)sc1[se]c3ccccc3c12] | −5.55 | −0.88 | −4.67 | 1.09 | 423 |
| 6. | 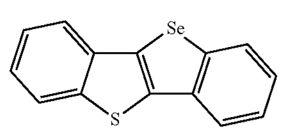 | −5.52 | −1.28 | −4.24 | 0.16 | 467 |
| 7. | 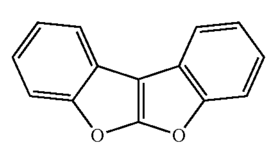 [SMILES: c1ccc2c(c1)oc1oc3ccccc3c12] | −5.55 | −0.38 | −5.17 | 1.14 | 369 |

TABLE 1-continued

Calculated Energy Levels foe Molecules Containing the Core of Compounds of Formula I[a]

| Molecule # | Structure | HOMO (ev) | LUMO (ev) | HOMO – LUMO (ev) | Dipole (Debye) | Calc. T1 (nm) |
|---|---|---|---|---|---|---|
| 8. | 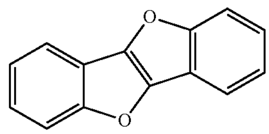 | −5.52 | −1.10 | −4.42 | 0.00 | 451 |
| 9. | 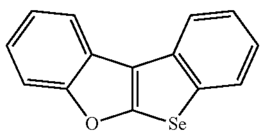 [SMILES: c1ccc2c(c1)oc1[se]c3ccccc3c12] | −5.51 | −0.64 | −4.87 | 1.00 | 401 |
| 10. | 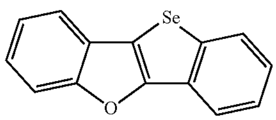 | −5.50 | −1.18 | −4.32 | 0.21 | 461 |
| 11. | 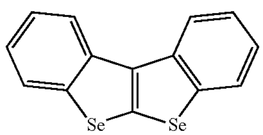 [SMILES: c1ccc2c(c1)[se]c1[se]c3ccccc3c12] | −5.51 | −0.90 | −4.61 | 0.88 | 428 |
| 12. | 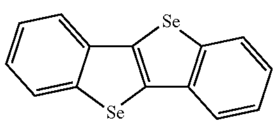 [SMILES: c1ccc2c(c1)[se]c1c3ccccc3[se]c21] | −5.47 | −1.30 | −4.17 | 0.00 | 473 |

[a]Calculation is based on DFT/B3LYP/6-31g(d) optimized geometry
b. The basis set used for Al, Bi, Zr, Ga, Ge, Y, Sc, Y, Ru, Zn, W, Mo, Os, Pt, Ir and Hf is cep-31g, the basis set used for all other elements is 6-31g(d)

From Table 1, we can see that the calculated triplet energy of molecule 1 and 7 are 418 nm and 369 nm, respectively. The experimental T1 of DBT is 415 nm and the experimental T1 of DBF is 417 nm. These results indicate that molecules containing the core of compounds of Formula I have potentially even higher triplet energy than DBT or DBF even with more fused cyclic rings and heteroatoms. These properties may be beneficial when compounds of Formula I are incorporated into OLED devices. Without being bound by theory, it is believed that compounds of Formula I would have better charge transport and charge stabilization properties as a result of the extended conjugation in compounds of Formula I in comparison to DBT- or DBF-type compounds. For example, the measured experimental T1 of Compound 3 was about 470 nm as predicted, which is very similar to the T1 (472 nm) of its DBT analog. Typically, increasing conjugation in host molecules results in the decrease of T1. However, it has unexpectedly been found that compounds of Formula I, which have increased conjugation in comparison to a DBT or DBF core actually maintain their T1 or in some instances have an even higher T1.

In one embodiment, at least one of $R_8$ and $R_9$ is independently selected from the group consisting of:

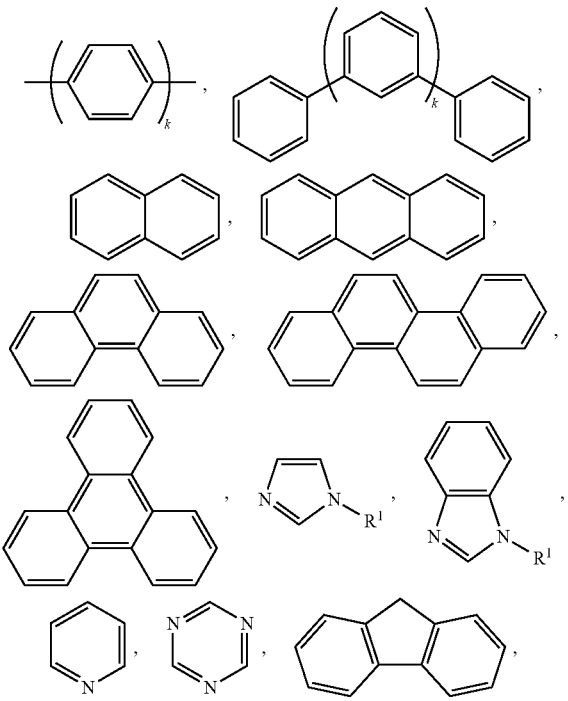

-continued

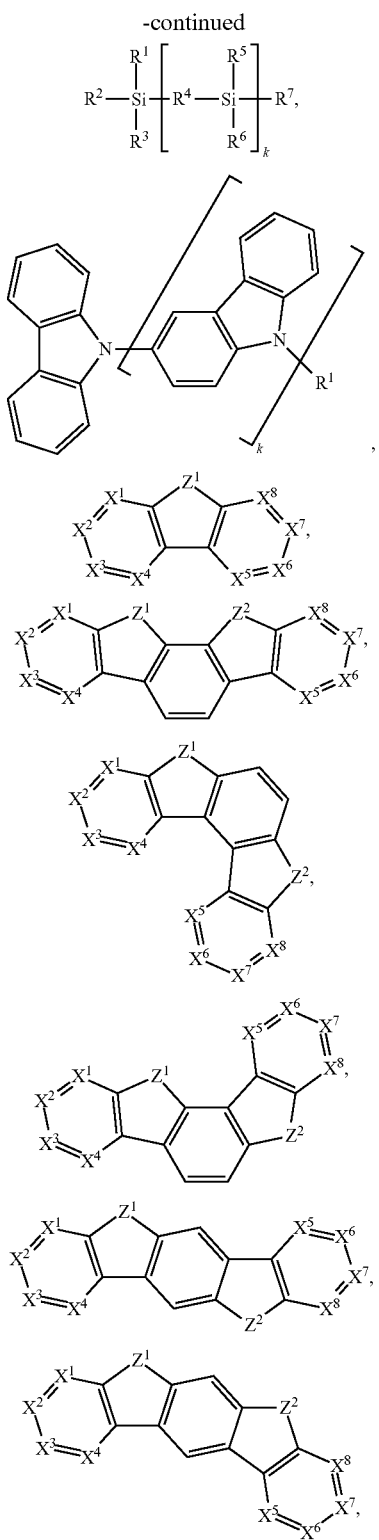

wherein $R^1$ to $R^7$ is independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof k is an integer from 0 to 20, $X^1$ to $X^8$ are independently selected from C, CH, and N, $Z^1$ and $Z^2$ is selected from $NR^1$, O, or S; and $R_8$ and $R_9$ may be further substituted.

In one embodiment, the compound has the formula:

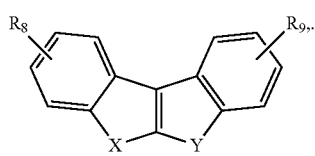

Formula II

In one embodiment, the compound has the formula:

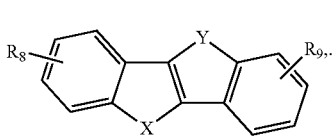

Formula III

In one embodiment, one of $Q_1$ to $Q_8$ is N.

In one embodiment, at least one of $R_8$ and $R_9$ has the formula:

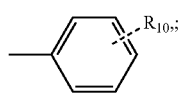

Formula IV wherein $R_{10}$ represents mono, di, tri, tetra substitution, or no substitution and wherein $R_{10}$ is selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

In one embodiment, $R_{10}$ represents mono-substitution and is selected from the group consisting of:

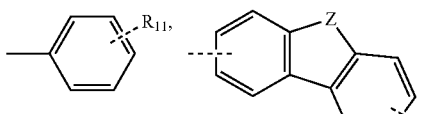

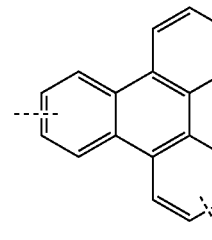

SiRR'R" and combinations thereof. Z is selected from the group consisting of NR, S, O, and Se. $R_{11}$, $R_{12}$, and $R_{13}$ represents mono, di, tri, tetra substitution, or no substitution. R, R', R", $R_{11}$, $R_{12}$, and $R_{13}$ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

When Z is N—R, $R_8$, $R_9$, or $R_{10}$ can connect to other portions of a compound of Formula I through the N or through a substituent bonded to the N, i.e. the R group attached to the N.

In one embodiment, at least one of $R_8$ and $R_9$ is independently selected from the group consisting of:

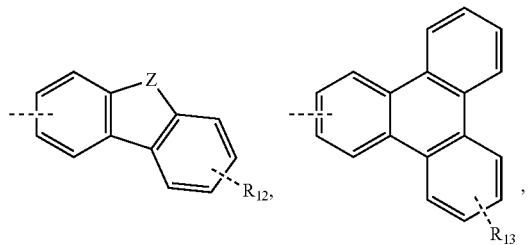

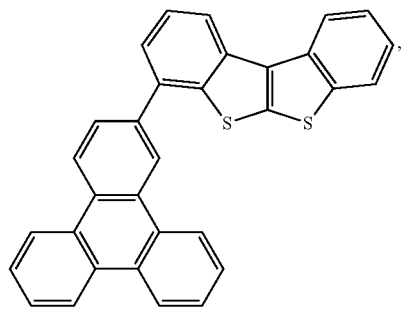

Compound 2

SiRR'R" and combinations thereof. Z is selected from the group consisting of NR, S, O, and Se. $R_{12}$ and $R_{13}$ represents mono, di, tri, tetra substitution, or no substitution, and R, R', R", $R_{12}$, and $R_{13}$ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

In one embodiment, X and Y are S.

In one embodiment, at least one of $R_8$ and $R_9$ is

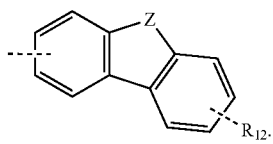

Compound 3

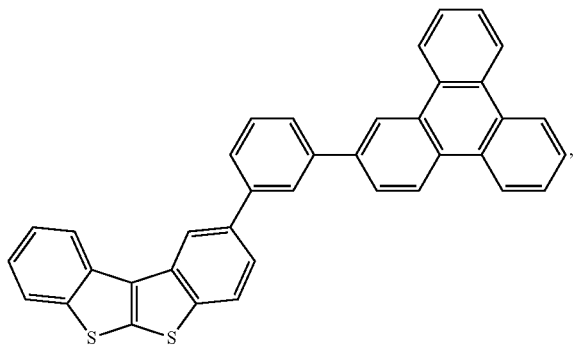

In one embodiment, at least one of $R_8$ and $R_9$ is

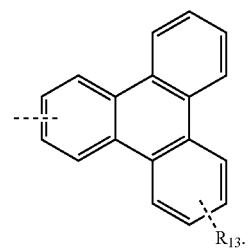

Compound 4

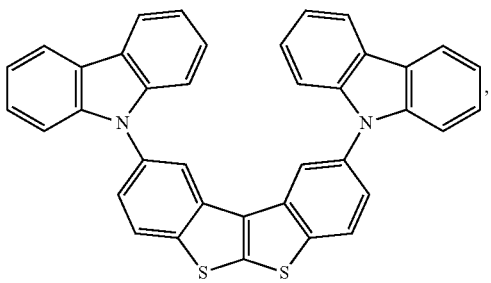

In one embodiment, at least one of $R_8$ and $R_9$ is SiRR'R". In another embodiment, $R_8$ is ortho or para to X, and wherein $R_9$ is ortho or para to Y. In one embodiment, $R_8$ is ortho or para to X, and wherein $R_9$ is ortho or para to Y. In one embodiment, $R_8$ is hydrogen or deuterium.

In one embodiment, the compound is selected from the group consisting of:

Compound 5

Compound 1

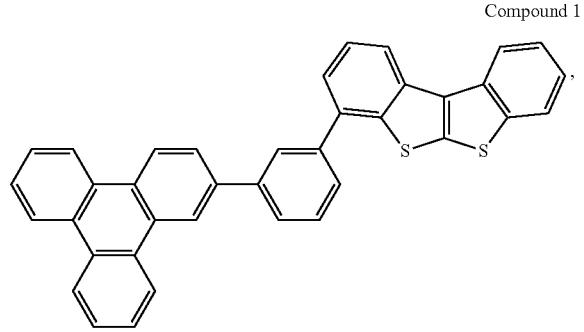

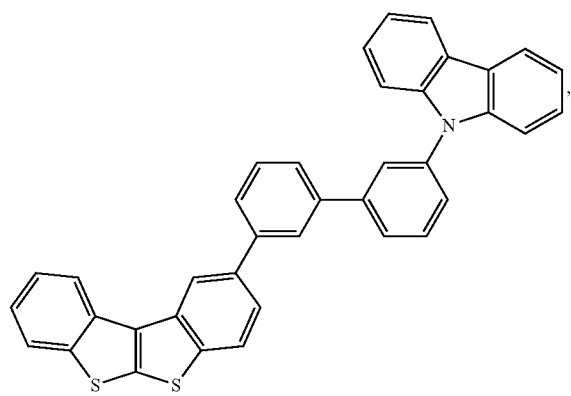

Compound 6
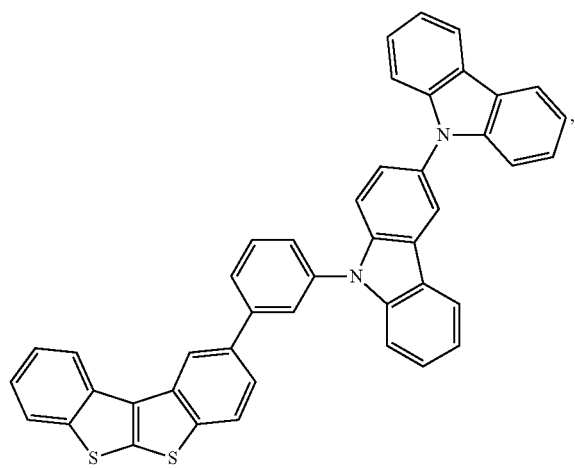
Compound 10
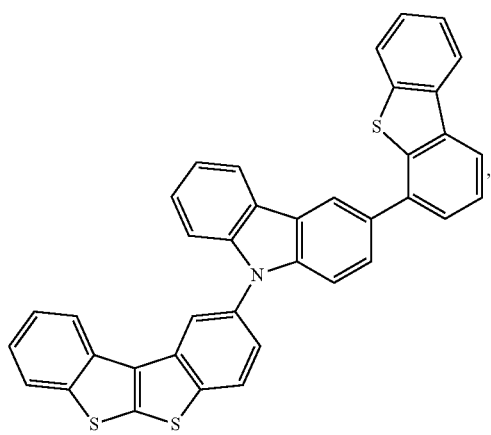
Compound 7
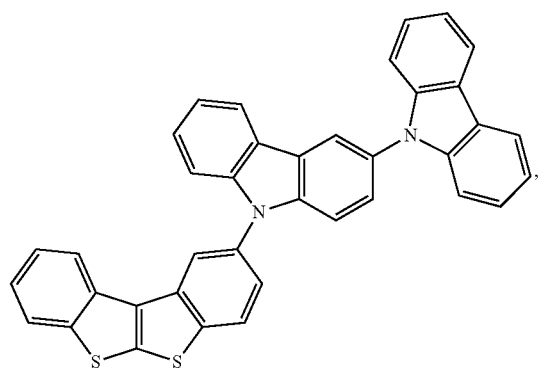
Compound 11
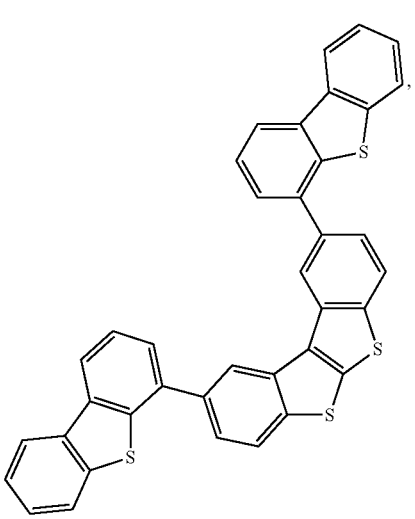
Compound 8
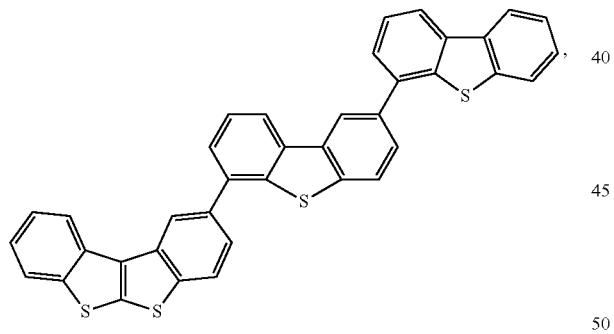
Compound 9
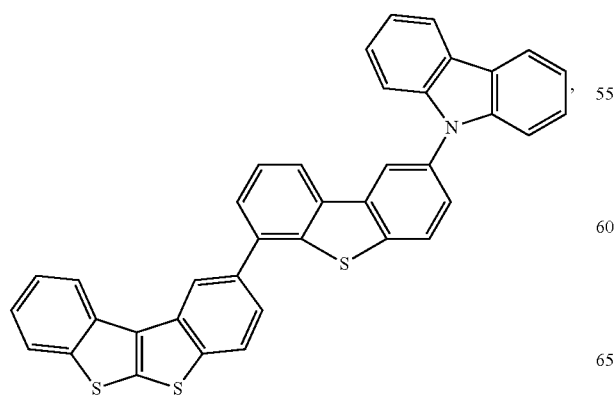
Compound 12
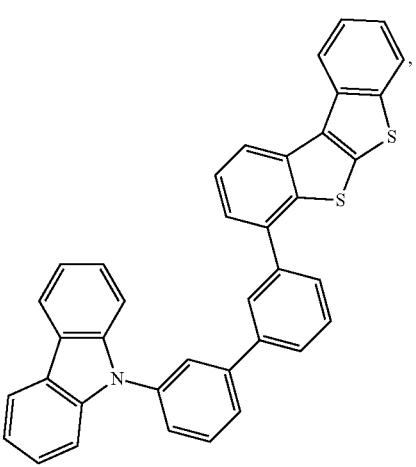

Compound 13
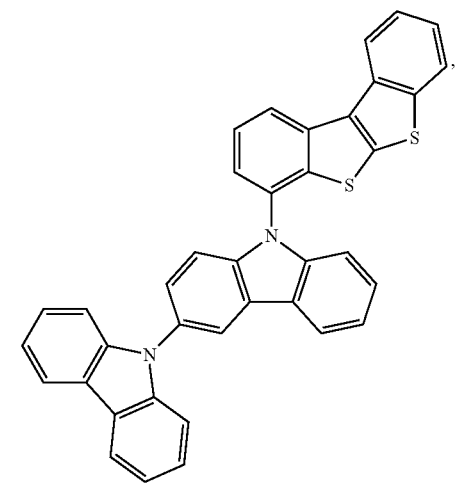
Compound 14
Compound 15
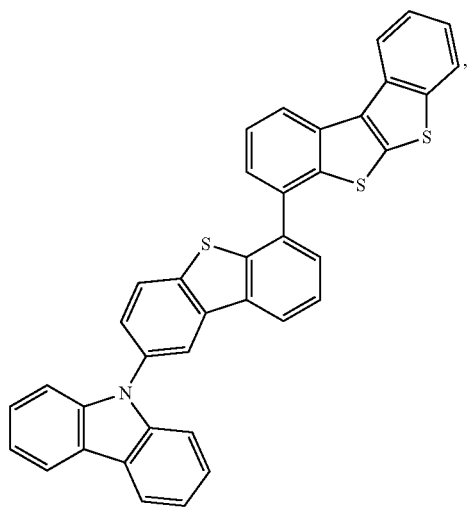
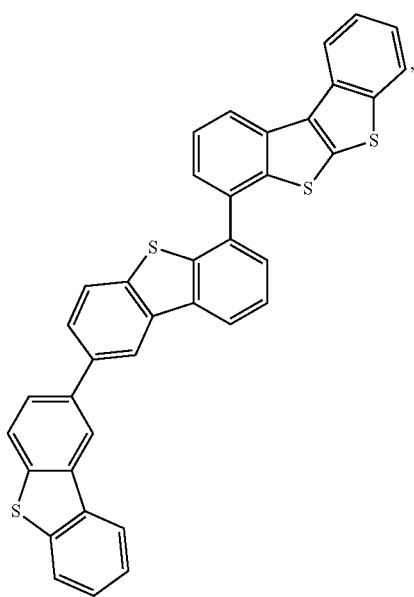
Compound 16
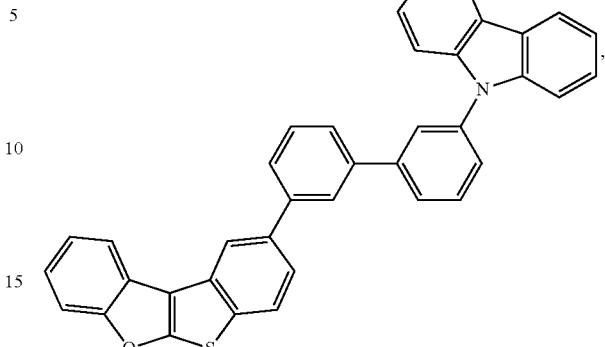
Compound 17
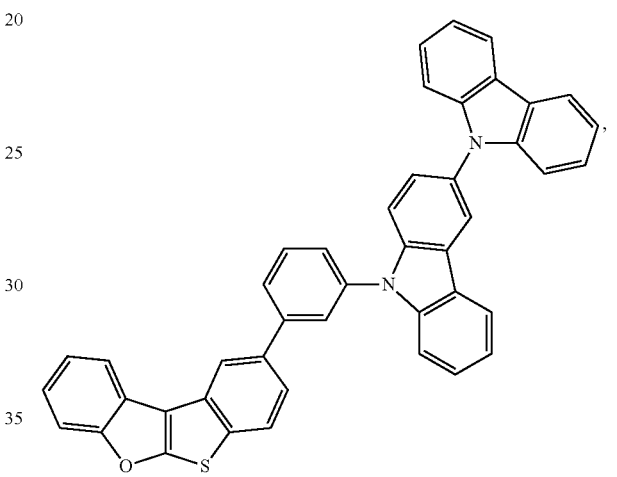
Compound 18
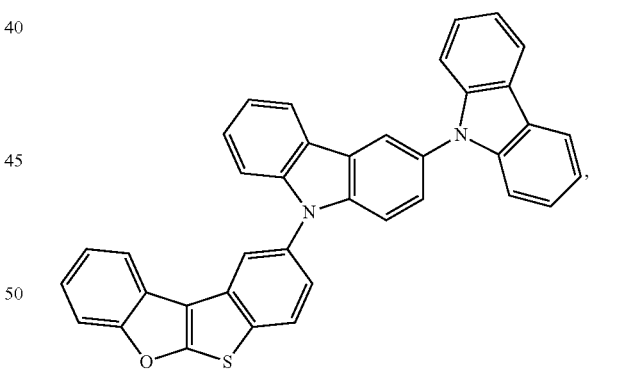
Compound 19
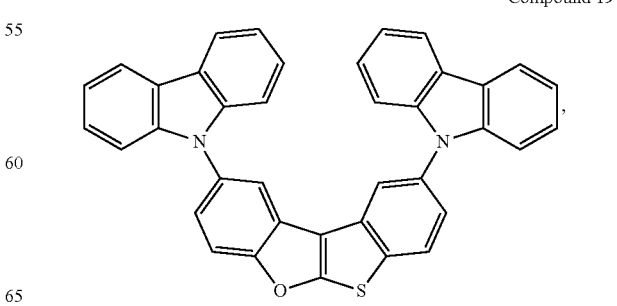

Compound 20
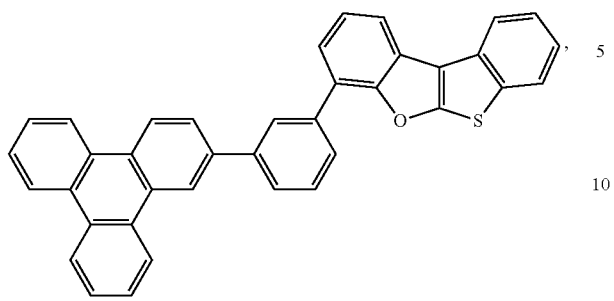
Compound 21
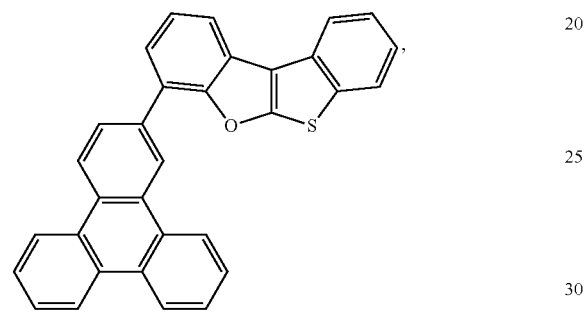
Compound 22
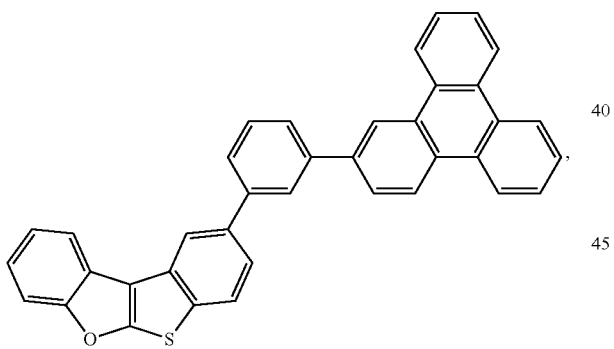
Compound 23
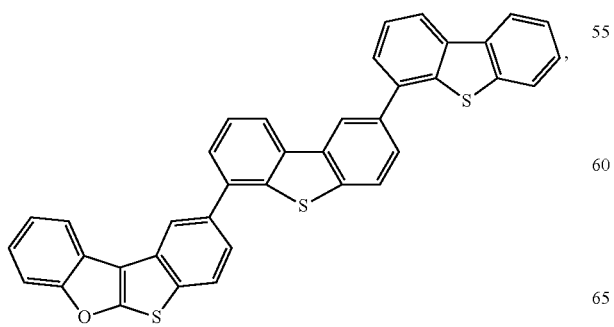
Compound 24
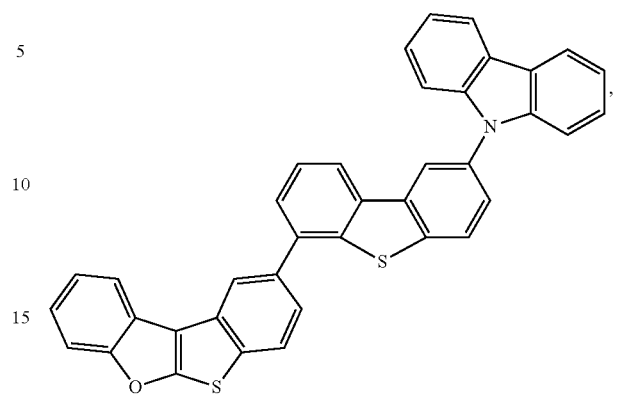
Compound 25
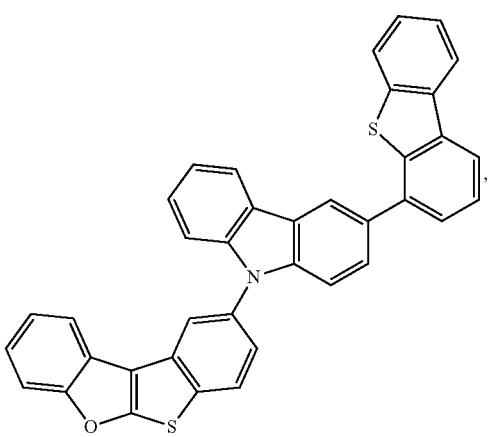
Compound 26
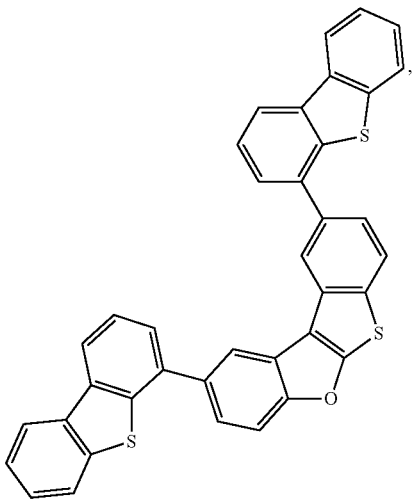

-continued
Compound 27
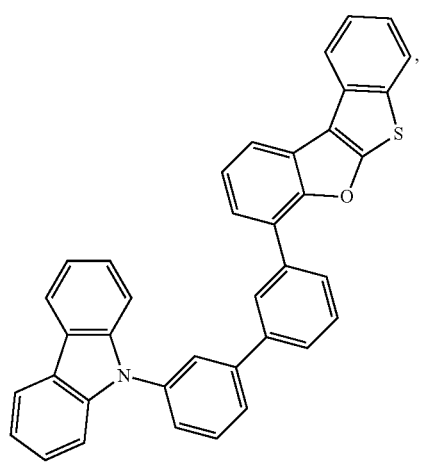
Compound 28
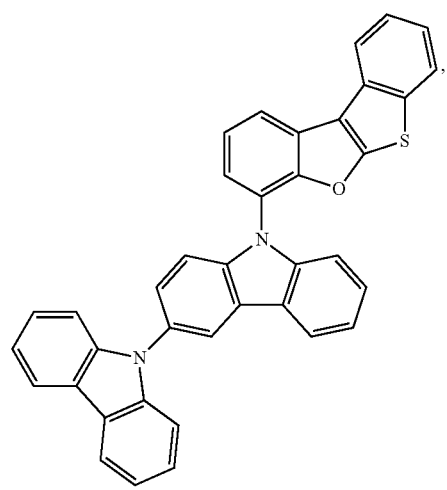
Compound 29
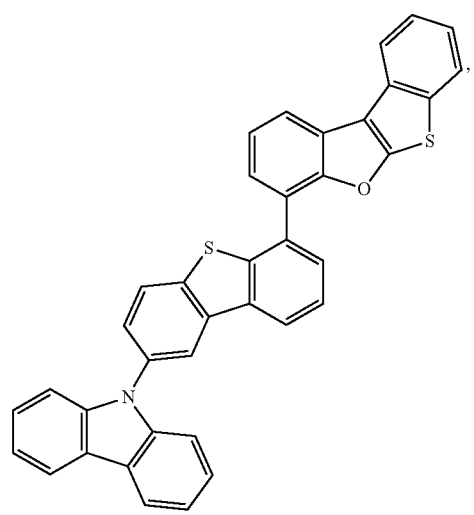
Compound 30
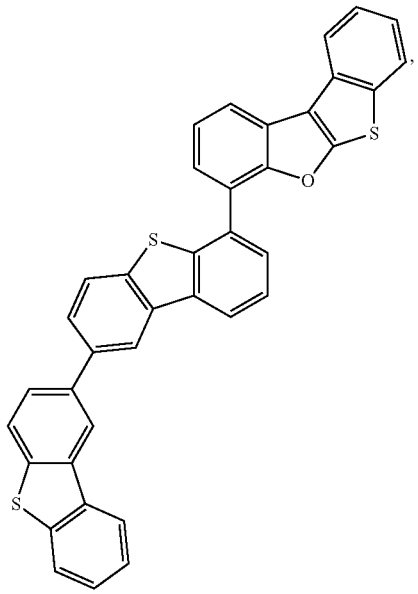
Compound 31
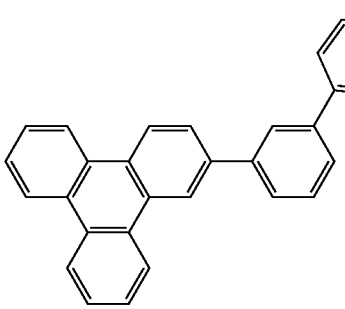
Compound 32
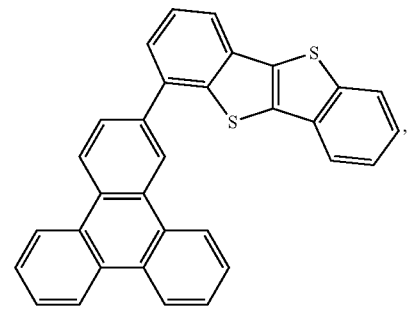
Compound 33
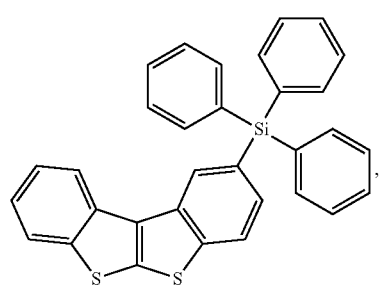

Compound 34
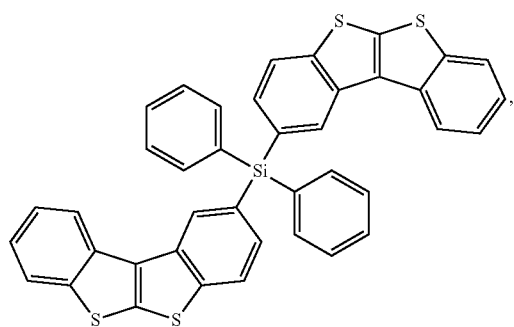
Compound 35
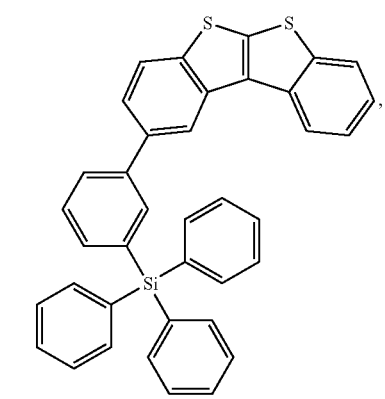
Compound 36
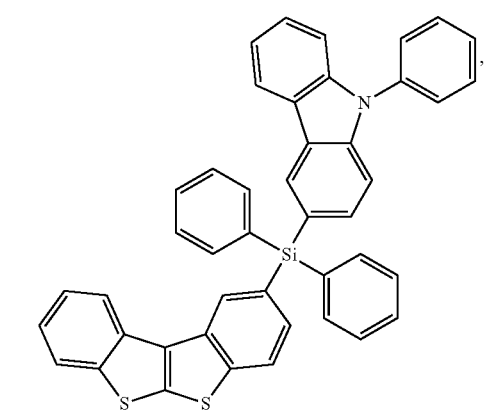
Compound 37
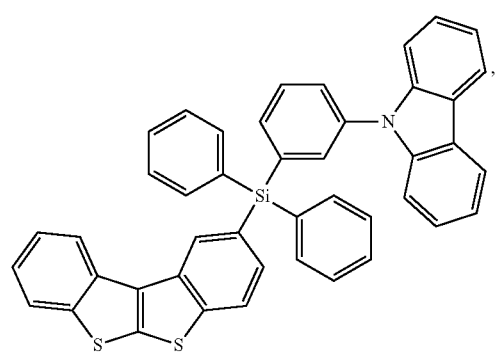
Compound 38
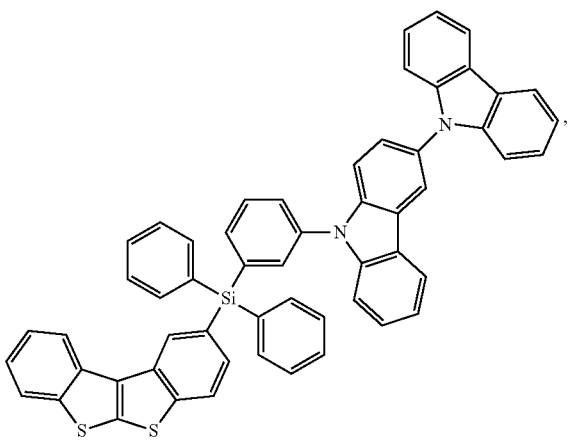
Compound 39
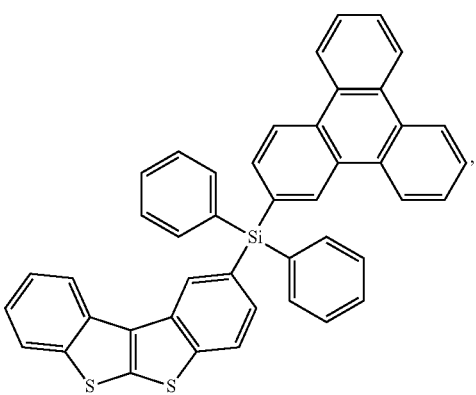
Compound 40
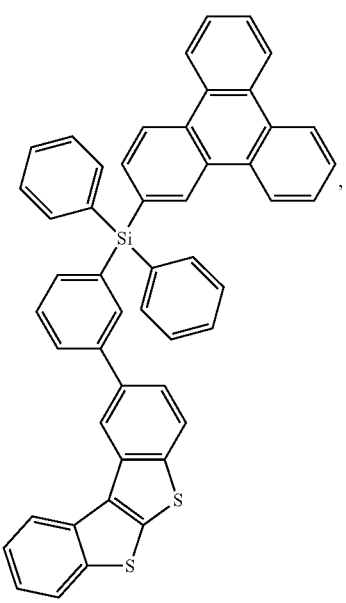

Compound 41
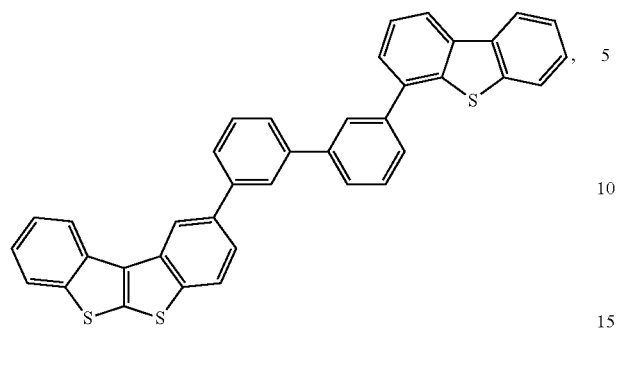
Compound 45
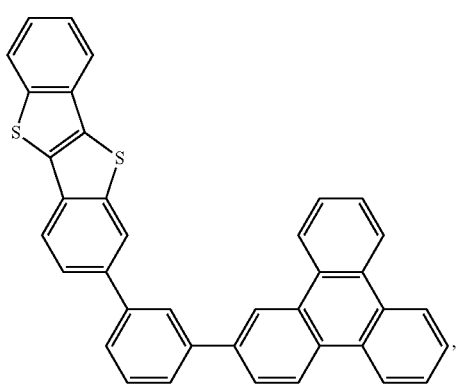
Compound 42
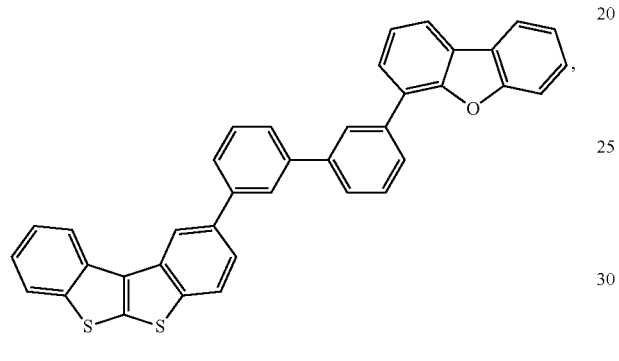
Compound 46
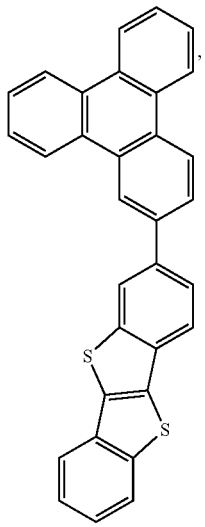
Compound 43
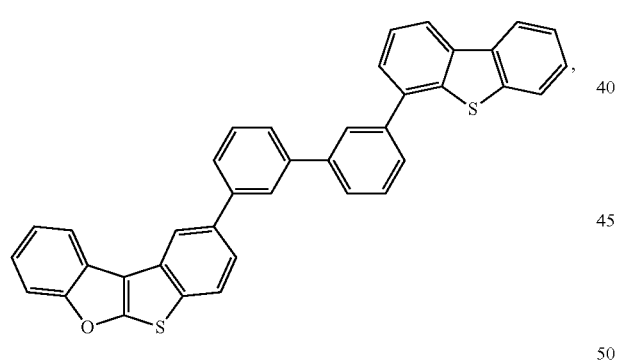
Compound 44
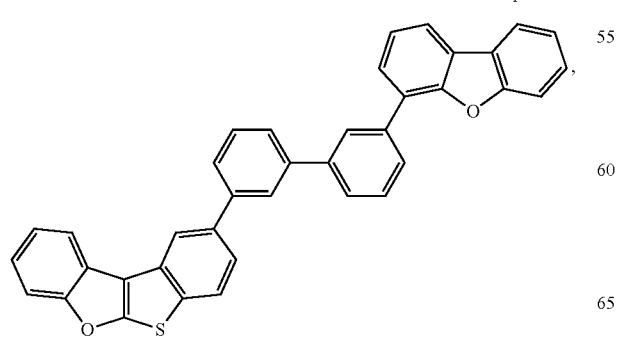
Compound 47
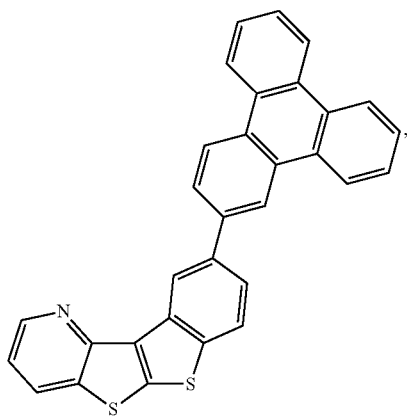

Compound 48

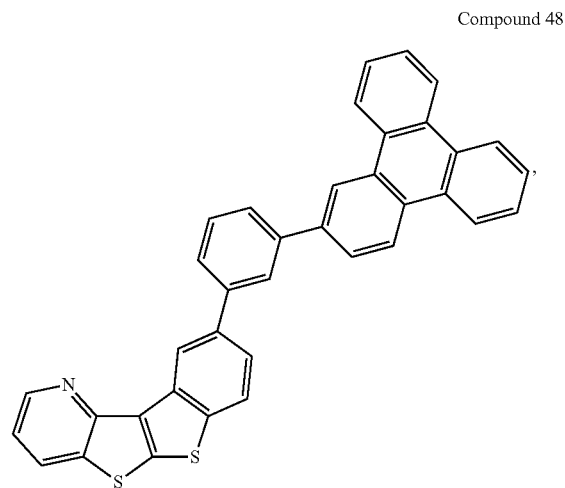

Compound 49

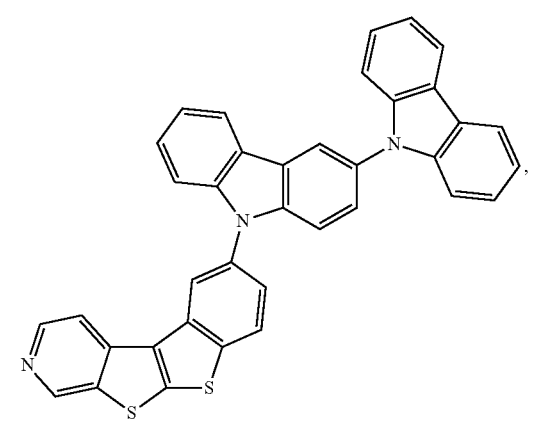

Compound 50

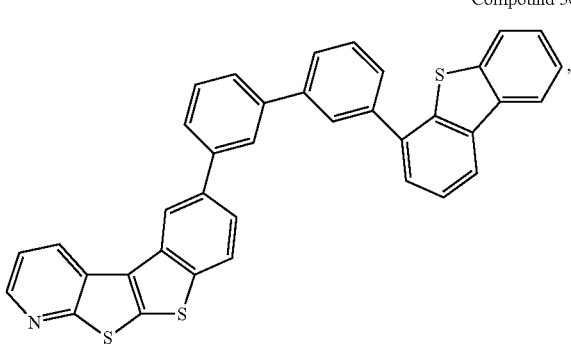

Compound 51

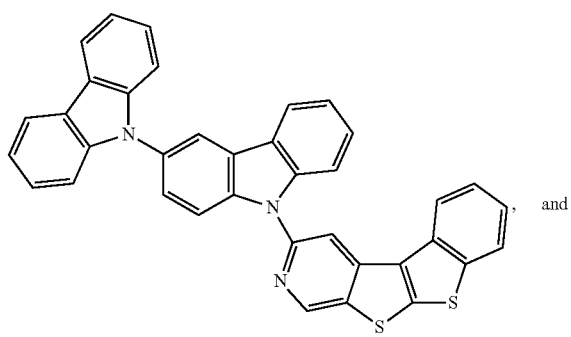

and

Compound 52

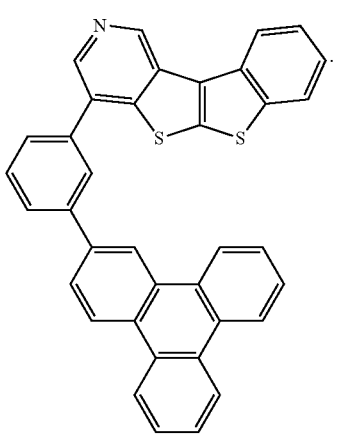

In one embodiment, a first device comprising an organic light emitting device, further comprising an anode, a cathode, and an organic layer, disposed between the anode and the cathode, comprising a compound having the formula:

Formula I

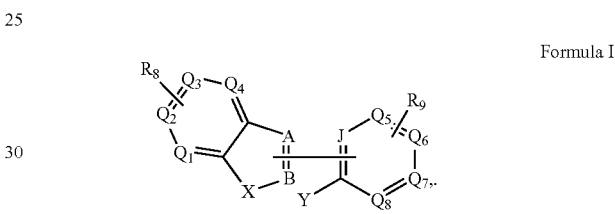

In the compound of Formula I, $Q_1$ to $Q_8$ are independently selected from CH and N, and wherein $Q_1$ to $Q_8$ may be further substituted. A is directly bonded to J and B is directly bonded to Y, or wherein A is directly bonded to Y and B is directly bonded to J. A, B, and J are carbon atoms. X and Y are independently selected from the group consisting of O, S, and Se. $R_8$ and $R_9$ independently represent mono, di, tri, tetra substitution, or no substitution. $R_8$ and $R_9$ are independently selected from the group consisting of deuterium, alkyl, cycloalkyl, arylalkyl, amino, silyl, germyl, alkenyl, cycloalkenyl, heteroalkenyl, alkynyl, aryl, heteroaryl, and combinations thereof, and at least one of $R_8$ and $R_9$ is not hydrogen or deuterium.

In one embodiment, the organic layer is an emissive layer and the compound of Formula I is a host. In one embodiment, the organic layer further comprises an emissive dopant.

In one embodiment, the emissive dopant is a transition metal complex having at least one ligand or part of the ligand if the ligand is more than bidentate selected from the group consisting of:

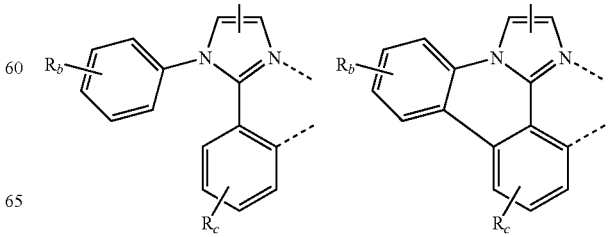

-continued

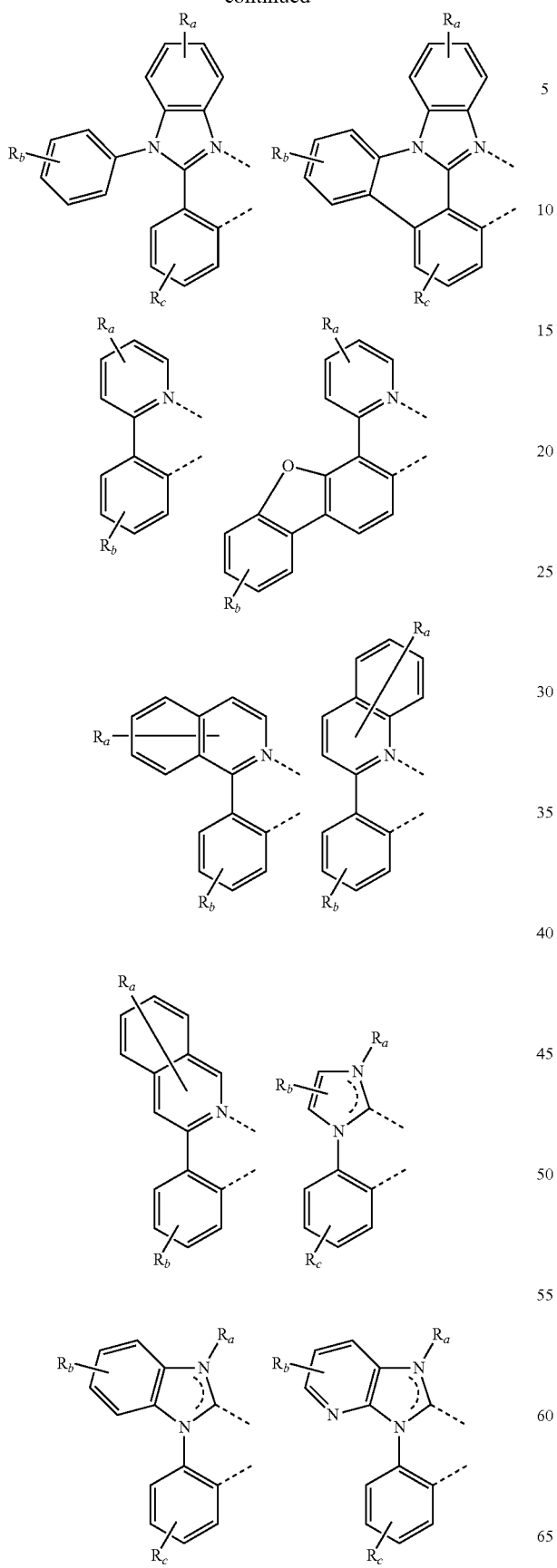
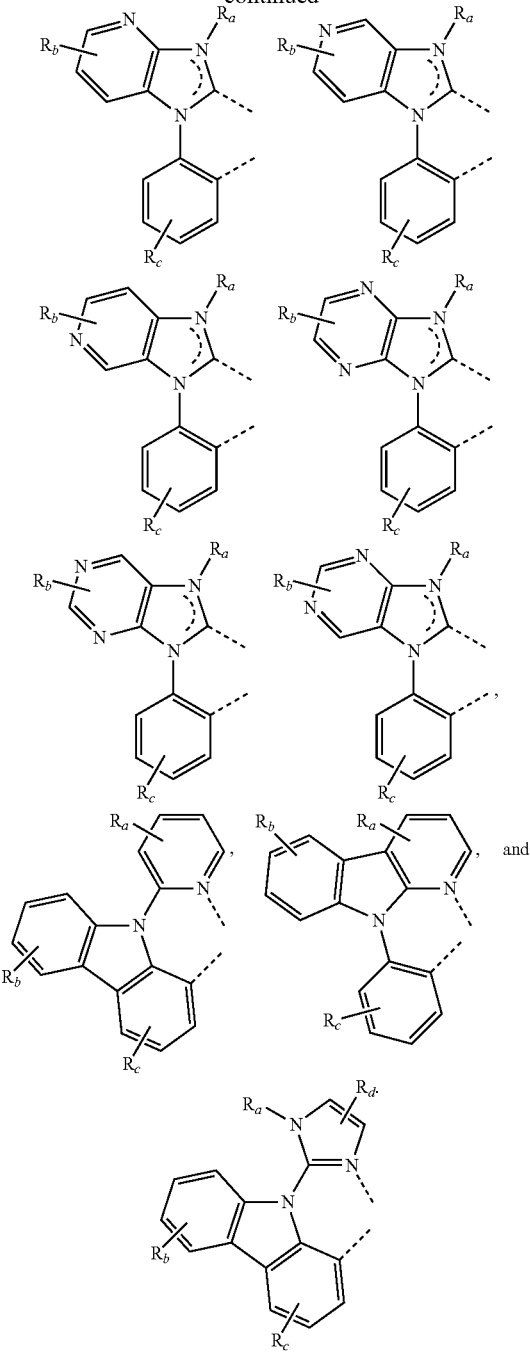

$R_a$, $R_b$, and $R_c$ may represent mono, di, tri or tetra substitutions, or no substitution, and $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two adjacent substituents of $R_a$, $R_b$, and $R_c$ are optionally joined to form a fused ring or form a multidentate ligand.

In one embodiment, the device further comprises a second organic layer that is a non-emissive layer and the compound having Formula I is a material in the second organic layer.

In one embodiment, the second organic layer is a blocking layer and the compound having Formula I is a blocking material in the second organic layer.

In one embodiment, the first device is a consumer product. In one embodiment, the first device is an organic light-emitting device. In one embodiment, the first device comprises a lighting panel.

DEVICE EXAMPLES

All example devices were fabricated by high vacuum (<$10^{-7}$ Torr) thermal evaporation (VTE). The anode electrode is 800 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound B or C as the hole injection layer (HIL), 300 Å of 4,4'-bis[N-(1-naphthyl)-N-phenylamino]biphenyl (NPD) as the hole transporting layer (HTL), 300 Å of a compound of Formula I doped in compound D as host with 12, 15, or 20 wt % of an Ir phosphorescent compound as the emissive layer (EML), 100 Å of Compound D or E as block layer (BL), 400 Å of $Alq_3$ (tris-8-hydroxyquinoline aluminum) as the ETL.

The device structure and data are summarized in Table 2 and Table 3 from those devices. As used herein, Compounds A, B, C, D and E have the following structures:

Compound A

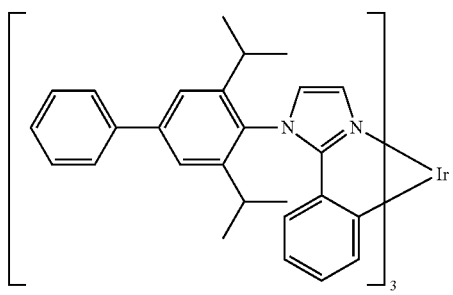

Compound B

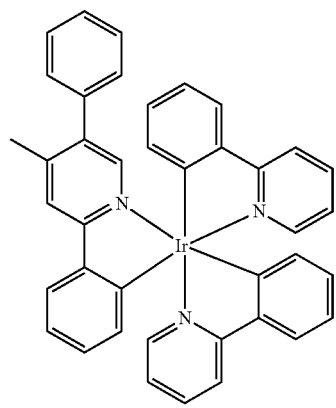

Compound C

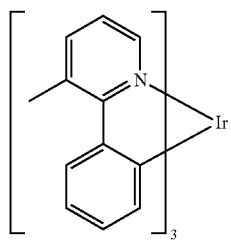

Compound D

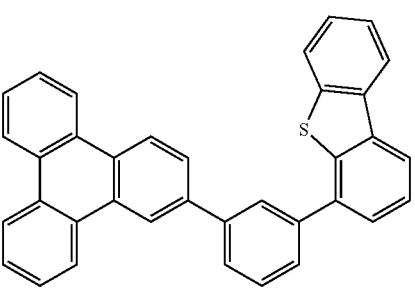

Compound E

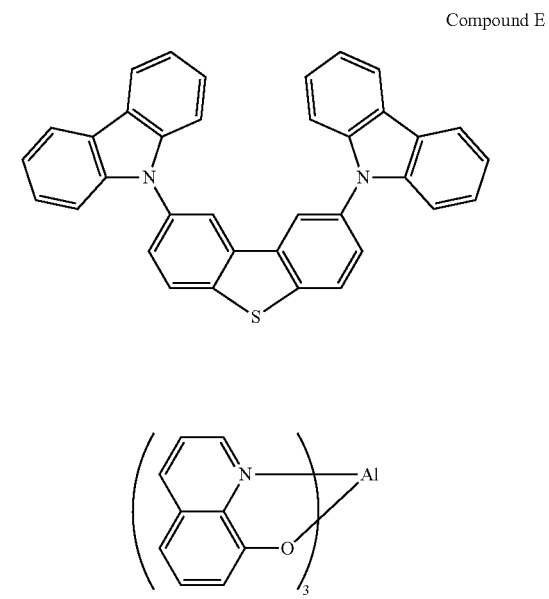

Alq

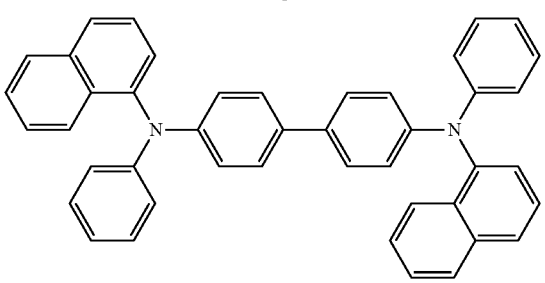

NPD

TABLE 2

Device Structures of Devices Incorporating Compounds of Formula I

| Example | HIL | HTL | EML (300 Å, doping %) | BL | ETL |
|---|---|---|---|---|---|
| Example 1 | Compound B 100 Å | NPD 300 Å | Compound 41 12% | Compound B Compound 41 100 Å | Alq 400 Å |
| Example 2 | Compound B 100 Å | NPD 300 Å | Compound 41 12% | Compound B Compound D 100 Å | Alq 400 Å |
| Example 3 | Compound B 100 Å | NPD 300 Å | Compound 41 12% | Compound B None | Alq 450 Å |
| Example 4 | Compound B 100 Å | NPD 300 Å | Compound 3 12% | Compound B Compound 3 100 Å | Alq 400 Å |
| Example 5 | Compound B 100 Å | NPD 300 Å | Compound 3 12% | Compound B Compound D 100 Å | Alq 400 Å |
| Example 6 | Compound B 100 Å | NPD 300 Å | Compound 3 12% | Compound B None | Alq 450 Å |
| Example 7 | Compound C 100 Å | NPD 300 Å | Compound 7 15% | Compound A Compound 7 100 Å | Alq 400 Å |
| Example 8 | Compound C 100 Å | NPD 300 Å | Compound 7 15% | Compound A Compound E 100 Å | Alq 400 Å |
| Example 9 | Compound C 100 Å | NPD 300 Å | Compound 7 20% | Compound A Compound 7 100 Å | Alq 400 Å |
| Example 10 | Compound C 100 Å | NPD 300 Å | Compound 7 20% | Compound A Compound E 100 Å | Alq 400 Å |
| Comparative Example 1 | Compound B 100 Å | NPD 300 Å | Compound D 12% | Compound B Compound D 100 Å | Alq 400 Å |
| Comparative Example 2 | Compound B 100 Å | NPD 300 Å | Compound D 12% | Compound B None | Alq 450 Å |

TABLE 3

VTE Device Data for Compounds of Formula I

| | x | y | $\lambda_{max}$ (nm) | FWHM (nm) | Voltage (V) | LE (Cd/A) | EQE (%) | PE (lm/W) |
|---|---|---|---|---|---|---|---|---|
| Example 1 | 0.319 | 0.628 | 522 | 64 | 6.4 | 45.5 | 12.6 | 22.1 |
| Example 2 | 0.321 | 0.628 | 522 | 66 | 5.8 | 62.9 | 17.4 | 33.8 |
| Example 3 | 0.318 | 0.628 | 522 | 64 | 7.5 | 15.2 | 4.2 | 6.4 |
| Example 4 | 0.348 | 0.612 | 528 | 74 | 6.4 | 43.5 | 12 | 21.5 |
| Example 5 | 0.365 | 0.602 | 532 | 78 | 6.9 | 33.9 | 9.4 | 15.3 |
| Example 6 | 0.359 | 0.605 | 528 | 76 | 8 | 19 | 5.3 | 7.5 |
| Example 7 | 0.187 | 0.421 | 476 | 60 | 9.4 | 26.8 | 11.2 | 9.0 |
| Example 8 | 0.185 | 0.414 | 474 | 60 | 7.9 | 31.8 | 13.4 | 12.6 |
| Example 9 | 0.184 | 0.415 | 476 | 60 | 8.2 | 28.6 | 12.1 | 10.9 |
| Example 10 | 0.180 | 0.406 | 474 | 58 | 6.9 | 39.2 | 16.9 | 17.7 |
| Comparative Example 1 | 0.324 | 0.626 | 522 | 66 | 6.8 | 62.2 | 17.2 | 28.9 |
| Comparative Example 2 | 0.323 | 0.626 | 522 | 66 | 7.6 | 24.7 | 6.8 | 10.2 |

Table 3 is a summary of the device data. The luminous efficiency (LE), external quantum efficiency (EQE) and power efficiency (PE) were measured at 1000 nits. Advantageously, the data indicates that the hosts containing benzo[b]benzo[4,5]thieno[3,2,d]thiophene core can be used as either green emitter hosts (Compound 3 and 41) or as blue emitter hosts (Compound 7). Thus, compounds of Formula I are efficient hosts when used in devices intended to emit blue or green light. Additionally, no energy quenching was observed with the novel hosts in the blue device as expected.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but do not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

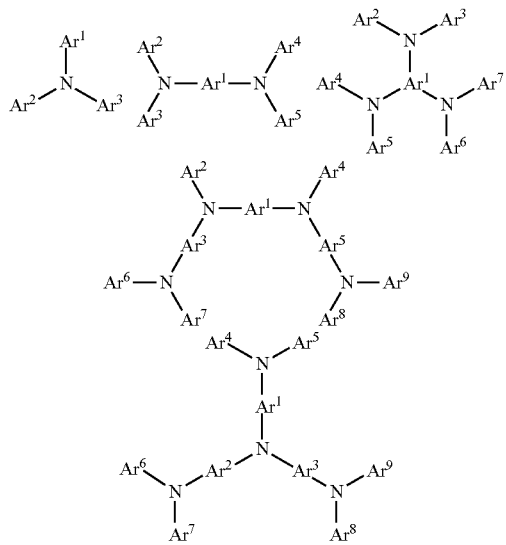

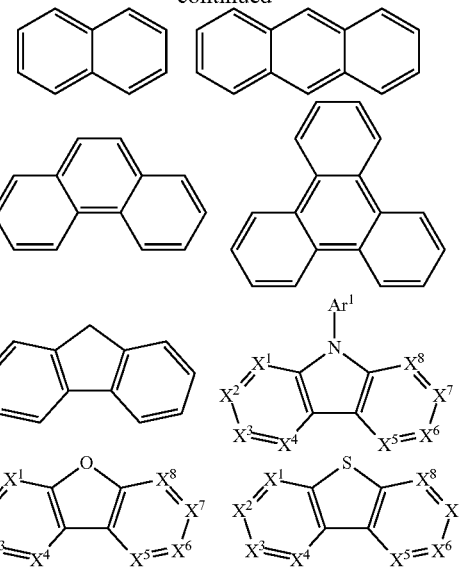

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

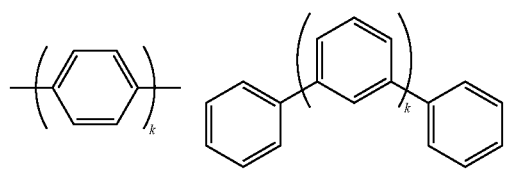

k is an integer from 1 to 20; $X^1$ to $X^8$ is C (including CH) or N; $Ar^1$ has the same group defined above.

Examples of metal complexes used in HIL or HTL include, but not limit to the following general formula:

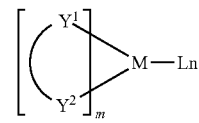

M is a metal, having an atomic weight greater than 40; ($Y^1$-$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$-$Y^2$) is a 2-phenylpyridine derivative.

In another aspect, ($Y^1$-$Y^2$) is a carbene ligand.

In another aspect, M is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

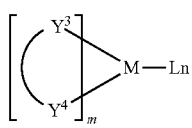

M is a metal; (Y³-Y⁴) is a bidentate ligand, Y³ and Y⁴ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

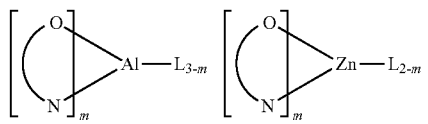

(O—N) is a bidentate ligand, having metal coordinated to atoms O and N.

In another aspect, M is selected from Ir and Pt.

In a further aspect, (Y³-Y⁴) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

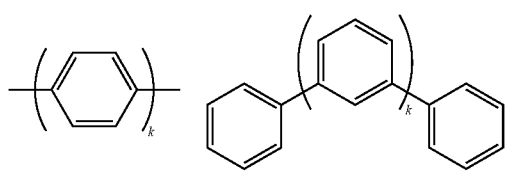

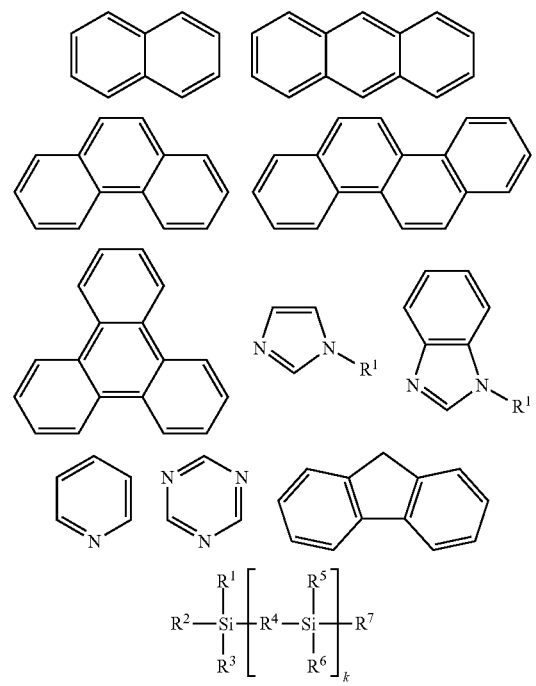

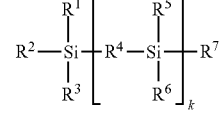

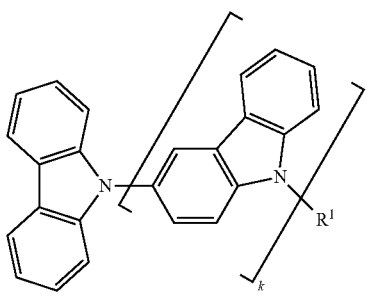

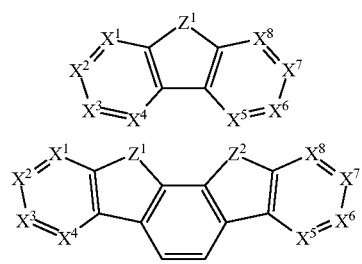

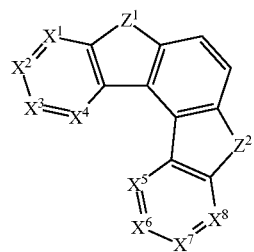

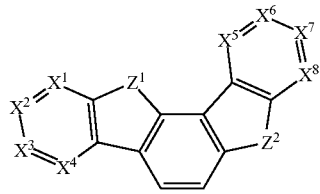

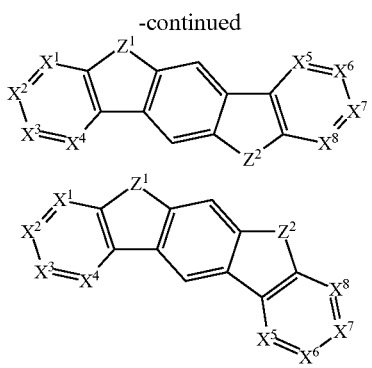

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

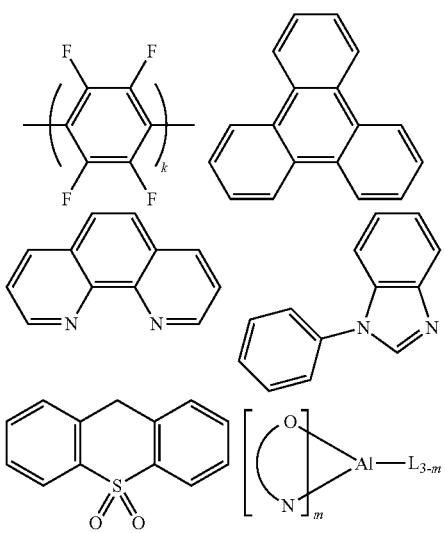

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

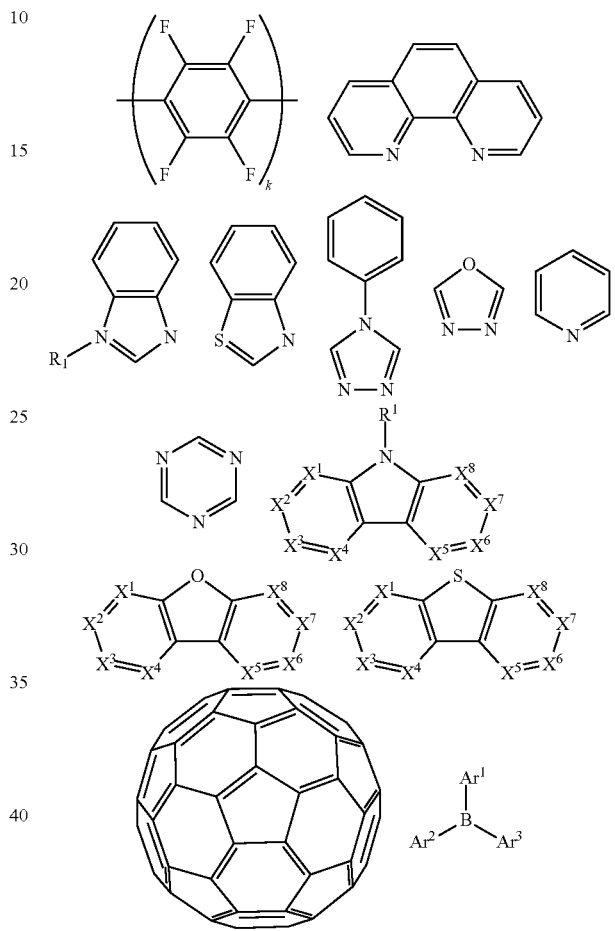

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

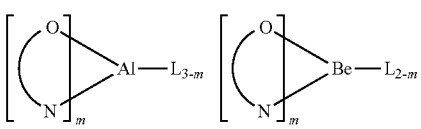

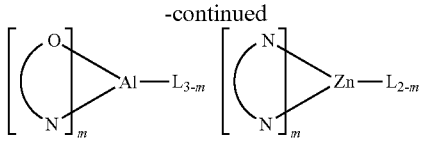

(O—N) or (N—N) is a bidentate ligand, having metal coordinated to atoms O, N or N, N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 2 lists non-limiting classes of materials, non-limiting examples of compounds for each class, and references that disclose the materials.

TABLE 2

| MATERIAL | EXAMPLES OF MATERIAL | PUBLICATIONS |
| --- | --- | --- |
| Hole injection materials | | |
| Phthalocyanine and porphryin compounds | | Appl. Phys. Lett. 69, 2160 (1996) |
| Starburst triarylamines | | J. Lumin. 72-74, 985 (1997) |
| CF$_x$ Fluorohydrocarbon polymer | $-(CH_xF_y)_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |

TABLE 2-continued

| MATERIAL | EXAMPLES OF MATERIAL | PUBLICATIONS |
| --- | --- | --- |
| Phosphonic acid and sliane SAMs | | US20030162053 |
| Triarylamine or polythiophene polymers with conductivity dopants | | EP1725079A1 |
| | and | |
| Organic compounds with conductive inorganic compounds, such as molybdenum and tungsten oxides | + MoO$_x$ | US20050123751<br>SID Symposium Digest, 37, 923 (2006)<br>WO2009018009 |

| MATERIAL | EXAMPLES OF MATERIAL | PUBLICATIONS |
| --- | --- | --- |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 2-continued
| MATERIAL | EXAMPLES OF MATERIAL | PUBLICATIONS |
| --- | --- | --- |
| Hole transporting materials | | |
| Triarylamines (e.g., TPD, α-NPD) | 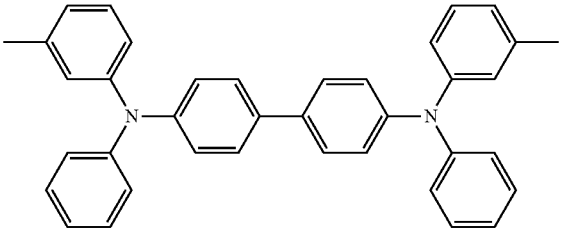 | Appl. Phys. Lett. 51, 913 (1987) |
| | 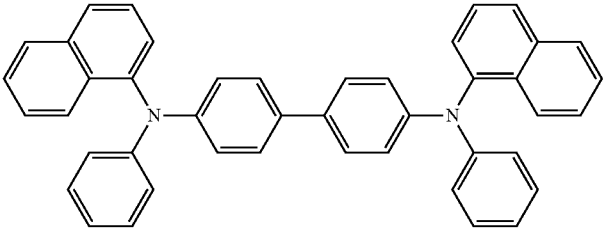 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 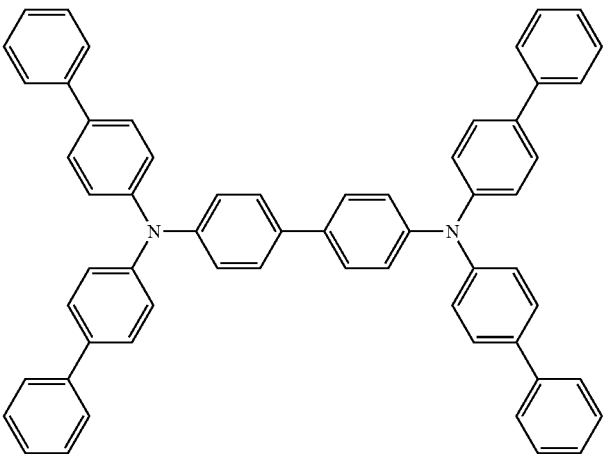 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 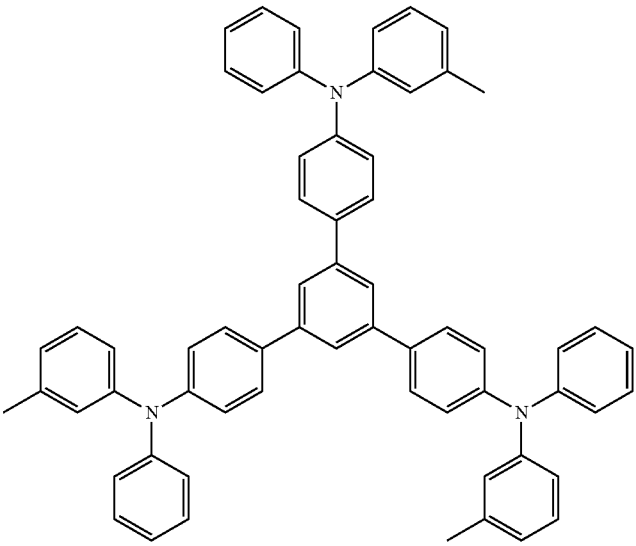 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 2-continued
| MATERIAL | EXAMPLES OF MATERIAL | PUBLICATIONS |
|---|---|---|
| | 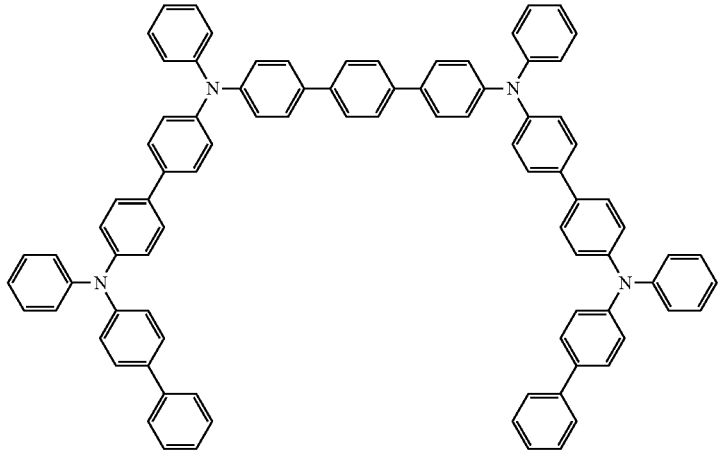 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| | 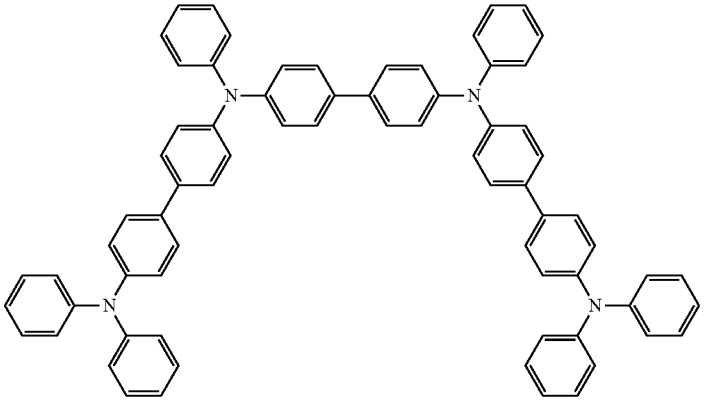 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triaylamine on spirofluorene core | 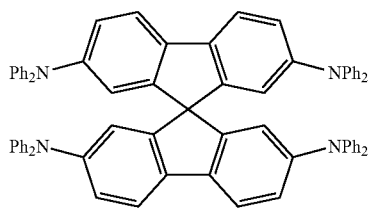 | Synth. Met. 91, 209 (1997) |
| Arylamine carbazole compounds | 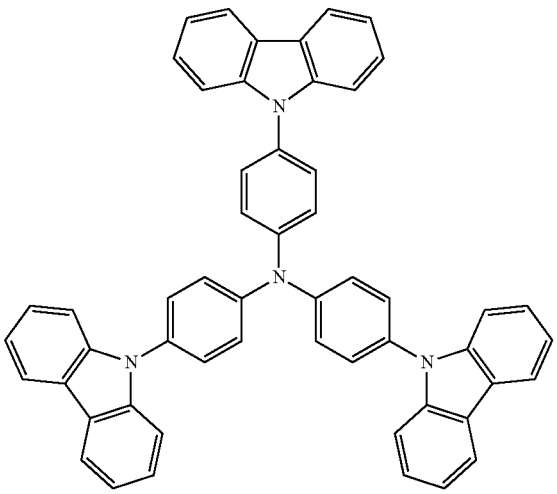 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 2-continued
| MATERIAL | EXAMPLES OF MATERIAL | PUBLICATIONS |
|---|---|---|
| Triarylamine with (di)benzothiophene/ (di)benzofuran | 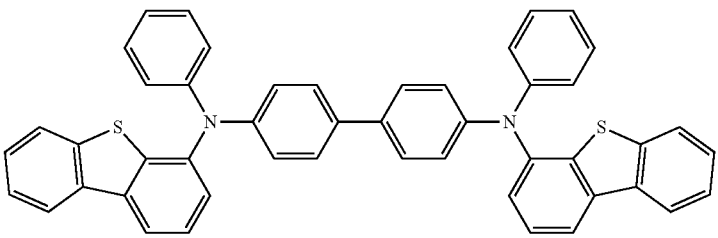 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 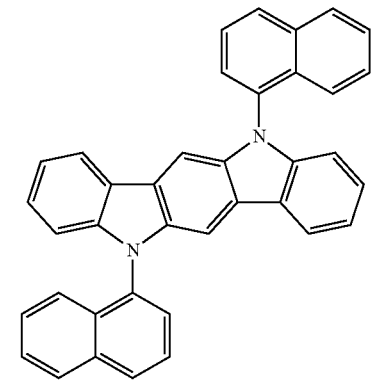 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 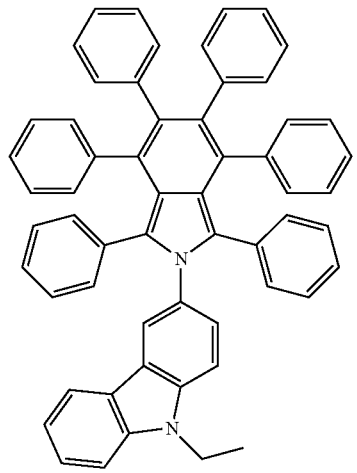 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 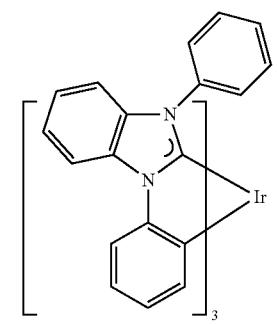 | US20080018221 |

TABLE 2-continued

| MATERIAL | EXAMPLES OF MATERIAL | PUBLICATIONS |
|---|---|---|
| Phosphorescent OLED host materials | | |
| Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 2-continued
| MATERIAL | EXAMPLES OF MATERIAL | PUBLICATIONS |
| --- | --- | --- |
| Aromatic fused rings | 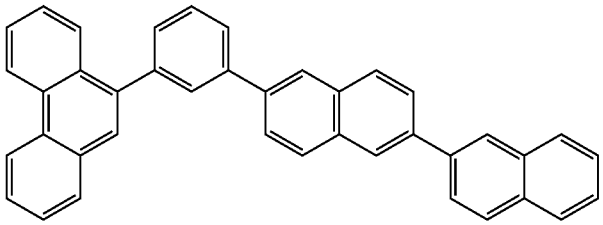 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 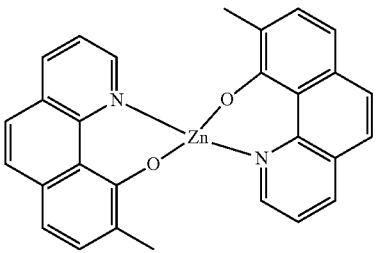 | WO2010056066 |
| Crysene based compounds | 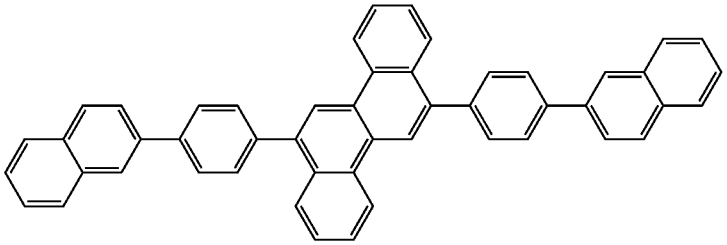 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
| Green hosts | | |
| Arylcarbazoles | 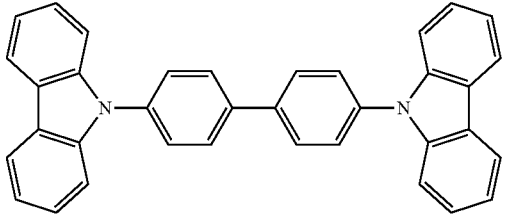 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 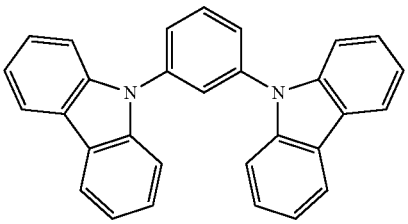 [SMILES: c1cc(-n2c3ccccc3c3ccccc32)cc(-n2c3ccccc3c3ccccc32)c1] | US20030175553 |
| | 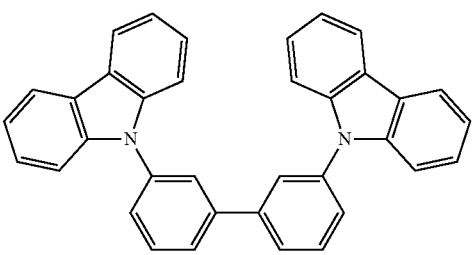 [SMILES: c1cc(-c2cccc(-n3c4ccccc4c4ccccc43)c2)cc(-n2c3ccccc3c3ccccc32)c1] | WO2001039234 |

TABLE 2-continued

| MATERIAL | EXAMPLES OF MATERIAL | PUBLICATIONS |
| --- | --- | --- |
| Aryltriphenylene compounds | | US20060280965 |
| | | US20060280965 |
| | | WO2009021126 |
| Poly-fused heteroaryl compounds | | US20090309488<br>US20090302743<br>US20100012931 |
| Donor acceptor type molecules | | WO2008056746 |

| MATERIAL | EXAMPLES OF MATERIAL | PUBLICATIONS |
|---|---|---|
| | 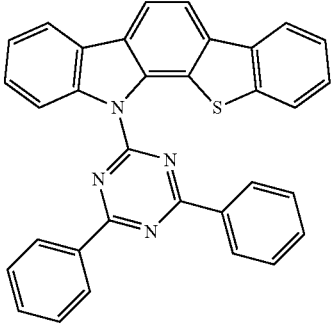 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 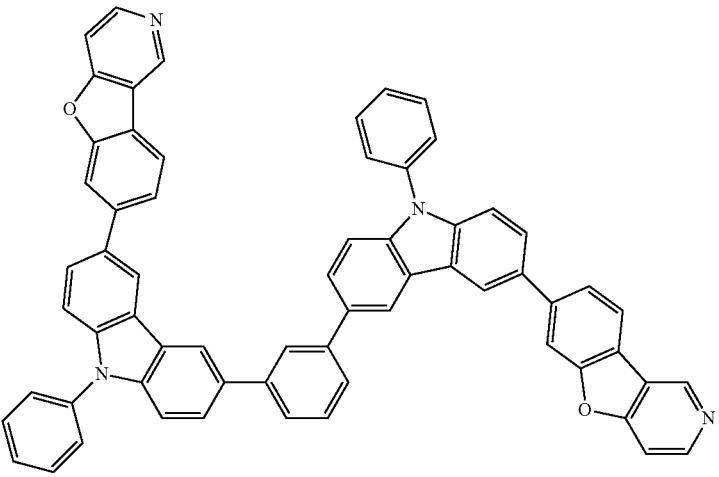 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 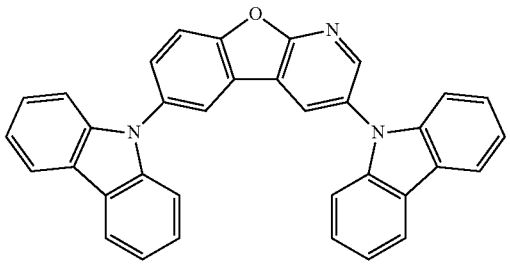 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 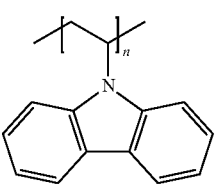 | Appl. Phys. Lett. 77, 2280 (2000) |
| Spirofluorene compounds | 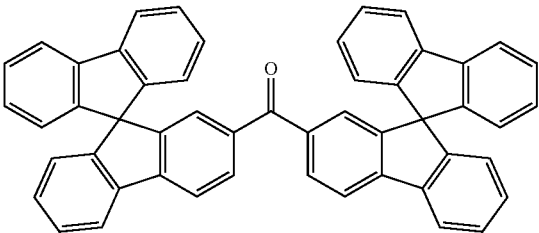 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 2-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 2-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| MATERIAL | EXAMPLES OF MATERIAL | PUBLICATIONS |
| --- | --- | --- |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 2-continued
| MATERIAL | EXAMPLES OF MATERIAL | PUBLICATIONS |
|---|---|---|
| | 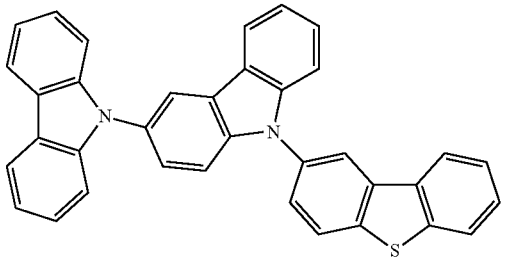 [SMILES: c1ccc2c(c1)sc1ccc(-n3c4ccccc4c4cc(-n5c6ccccc6c6ccccc65)ccc43)cc12] | WO2009086028 |
| | 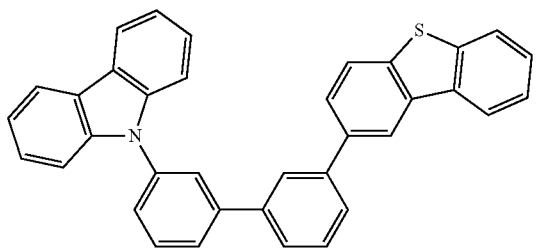 [SMILES: c1cc(-c2cccc(-n3c4ccccc4c4ccccc43)c2)cc(-c2ccc3sc4ccccc4c3c2)c1] | US20090030202, US20090017330 |
| | 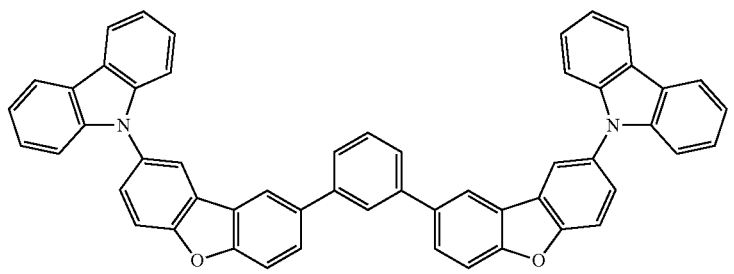 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 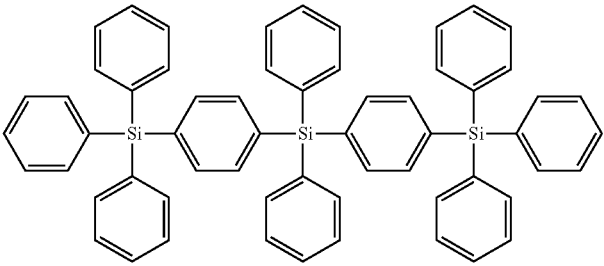 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 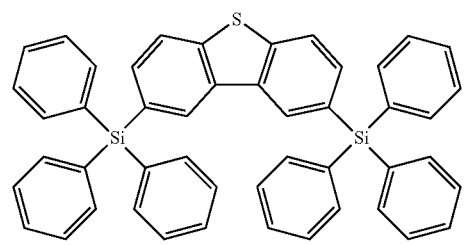 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 2-continued

| MATERIAL | EXAMPLES OF MATERIAL | PUBLICATIONS |
| --- | --- | --- |
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

TABLE 2-continued

| MATERIAL | EXAMPLES OF MATERIAL | PUBLICATIONS |
| --- | --- | --- |
| *Phosphorescent dopants* | | |
| *Red dopants* | | |
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |
| | | US2006835469 |
| | | US20060202194 |

| MATERIAL | EXAMPLES OF MATERIAL | PUBLICATIONS |
|---|---|---|
| | 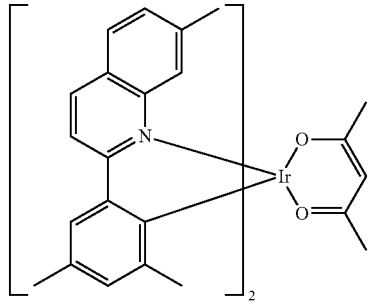 | US20060202194 |
| | 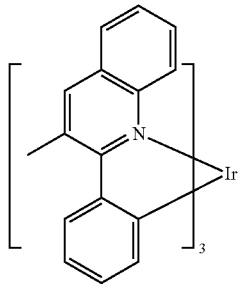 | US20070087321 |
| | 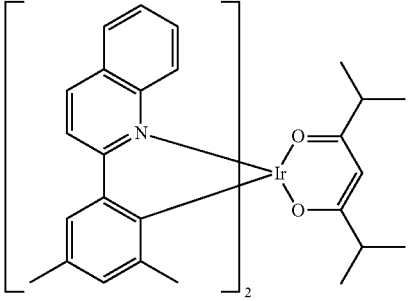 | US20080261076<br>US20100090591 |
| | 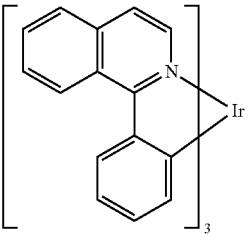 | US20070087321 |
| | 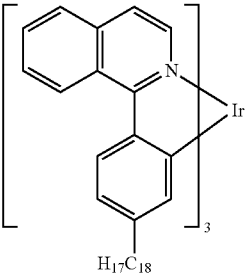 | Adv. Mater. 19, 739 (2007) |

| MATERIAL | EXAMPLES OF MATERIAL | PUBLICATIONS |
|---|---|---|
| | | WO2009100991 |
| | | WO2008101842 |
| | | U.S. Pat. No. 7,232,618 |
| Platinum(II) organometallic complexes | | WO2003040257 |
| | | US20070103060 |

TABLE 2-continued

| MATERIAL | EXAMPLES OF MATERIAL | PUBLICATIONS |
| --- | --- | --- |
| Osminum(III) complexes | | Chem. Mater. 17, 3532 (2005) |
| Ruthenium(II) complexes | | Adv. Mater. 17, 1059 (2005) |
| Rhenium (I), (II), and (III) complexes | | US20050244673 |

Green dopants

| | | |
| --- | --- | --- |
| Iridium(III) organometallic complexes | and its derivatives | Inorg. Chem. 40, 1704 (2001) |
| | | US20020034656 |

TABLE 2-continued
| MATERIAL | EXAMPLES OF MATERIAL | PUBLICATIONS |
|---|---|---|
| | 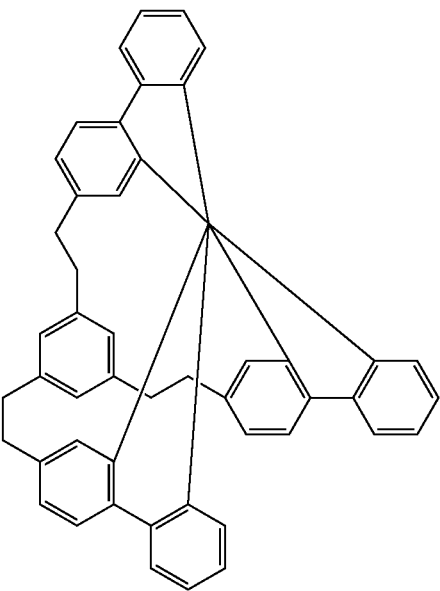 | U.S. Pat. No. 7,332,232 |
| | 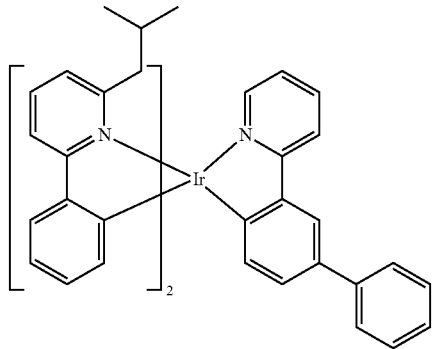 | US20090108737 |
| | 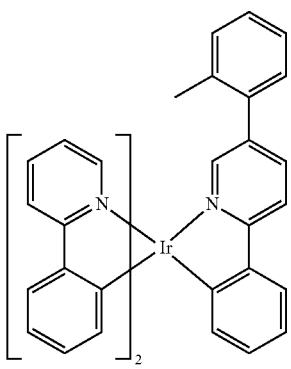 | WO2010028151 |

TABLE 2-continued

| MATERIAL | EXAMPLES OF MATERIAL | PUBLICATIONS |
|---|---|---|
| | | EP1841834B |
| | | US20060127696 |
| | | US20090039776 |
| | | U.S. Pat. No. 6,921,915 |
| | | US20100244004 |

TABLE 2-continued
| MATERIAL | EXAMPLES OF MATERIAL | PUBLICATIONS |
|---|---|---|
| | 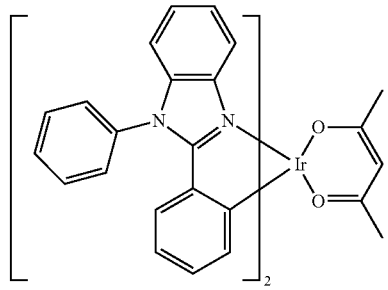 | U.S. Pat. No. 6,687,266 |
| | 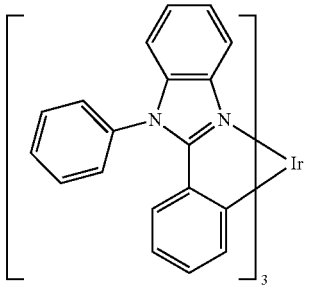 | Chem. Mater. 16, 2480 (2004) |
| | 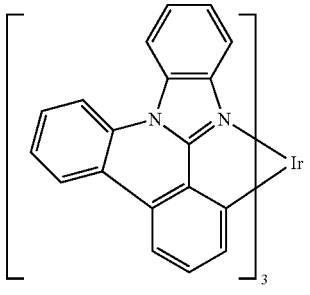 | US20070190359 |
| | 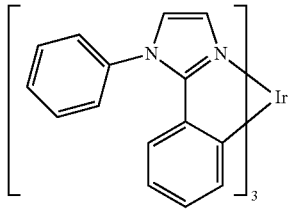 | US 20060008670 JP2007123392 |
| | 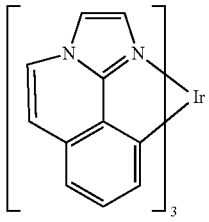 | WO2010086089, WO2011044988 |
| | 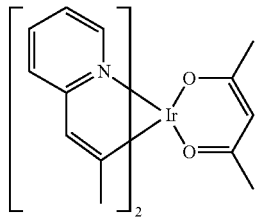 | Adv. Mater. 16, 2003 (2004) |

TABLE 2-continued

| MATERIAL | EXAMPLES OF MATERIAL | PUBLICATIONS |
|---|---|---|
| | | Angew. Chem. Int. Ed. 2006, 45, 7800 |
| | | WO2009050290 |
| | | US20090165846 |
| | | US20080015355 |
| | | US20010015432 |
| | | US20100295032 |

TABLE 2-continued
| MATERIAL | EXAMPLES OF MATERIAL | PUBLICATIONS |
|---|---|---|
| Monomer for polymeric metal organometallic compounds | 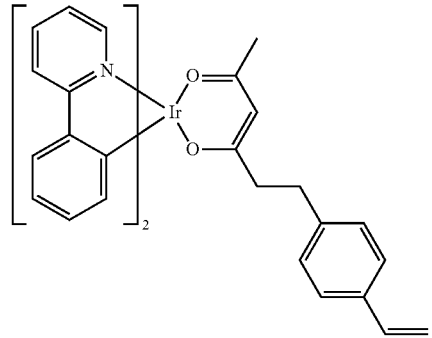 | U.S. Pat. No. 7,250,226, U.S. Pat. No. 7,396,598 |
| Pt(II) organometallic complexes, including polydentated ligands | 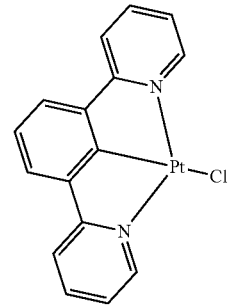 | Appl. Phys. Lett. 86, 153505 (2005) |
| | 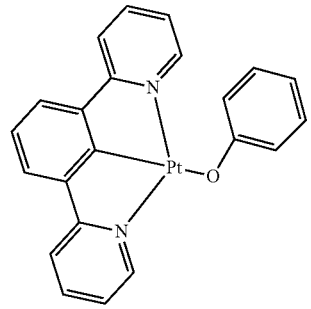 | Appl. Phys. Lett. 86, 153505 (2005) |
| | 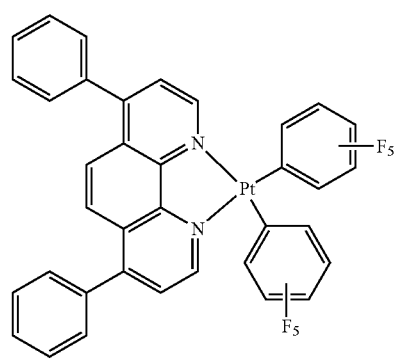 | Chem. Lett. 34, 592 (2005) |
| | 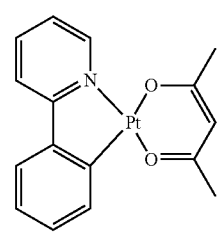 | WO2002015645 |

TABLE 2-continued

| MATERIAL | EXAMPLES OF MATERIAL | PUBLICATIONS |
| --- | --- | --- |
| | | US20060263635 |
| | | US20060182992<br>US20070103060 |
| Cu complexes | | WO2009000673 |
| | | US20070111026 |

TABLE 2-continued
| MATERIAL | EXAMPLES OF MATERIAL | PUBLICATIONS |
|---|---|---|
| Gold complexes | 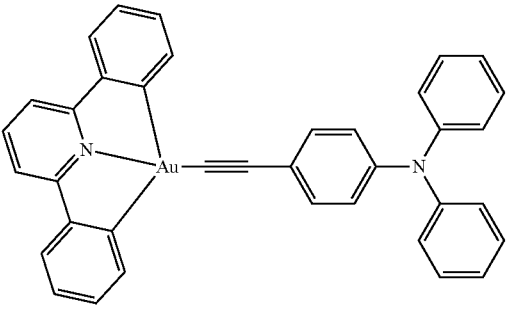 | Chem. Commun. 2906 (2005) |
| Rhenium(III) complexes | 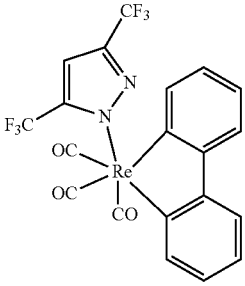 | Inorg. Chem. 42, 1248 (2003) |
| Osmium(II) complexes | 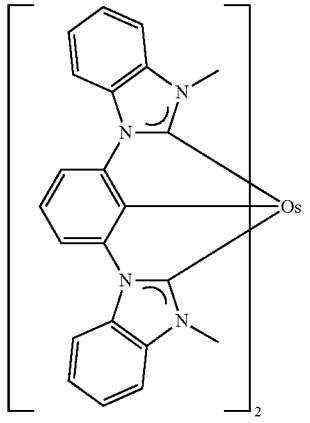 | U.S. Pat. No. 7,279,704 |
| Deuterated organometallic complexes | 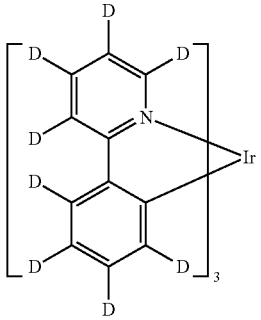 | US20030138657 |

TABLE 2-continued
| MATERIAL | EXAMPLES OF MATERIAL | PUBLICATIONS |
|---|---|---|
| Organometallic complexes with two or more metal centers | 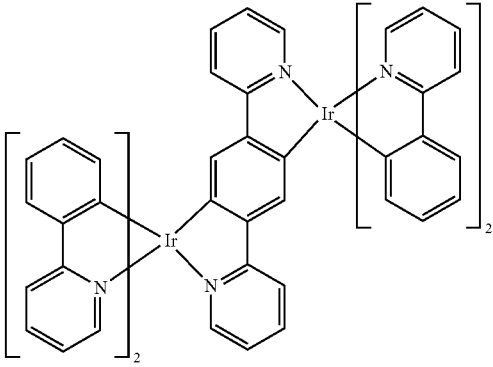 | US20030152802 |
| | 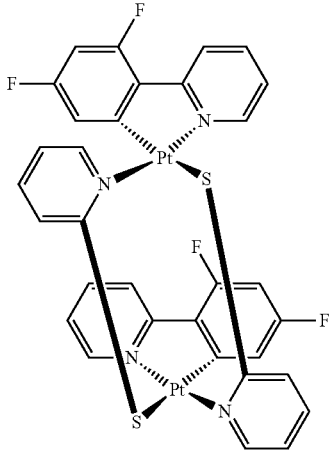 | U.S. Pat. No. 7,090,928 |
Blue dopants
| | | |
|---|---|---|
| Iridium(III) organometallic complexes | 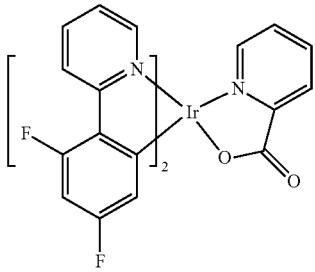 | WO2002002714 |
| | 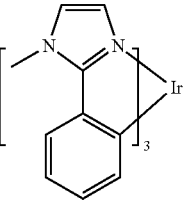 | WO2006009024 |
| | 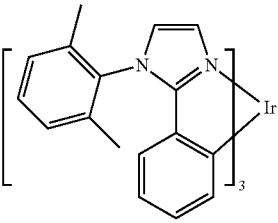 | US20060251923<br>US20110057559<br>US20110204333 |

TABLE 2-continued

| MATERIAL | EXAMPLES OF MATERIAL | PUBLICATIONS |
|---|---|---|
| | (structure) | U.S. Pat. No. 7,393,599, WO2006056418, US20050260441, WO2005019373 |
| | (structure) | U.S. Pat. No. 7,534,505 |
| | (structure) | WO2011051404 |
| | (structure) | U.S. Pat. No. 7,445,855 |
| | (structure) | US20070190359, US20080297033 US20100148663 |

TABLE 2-continued

| MATERIAL | EXAMPLES OF MATERIAL | PUBLICATIONS |
|---|---|---|
| | | U.S. Pat. No. 7,338,722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |

| MATERIAL | EXAMPLES OF MATERIAL | PUBLICATIONS |
|---|---|---|
| | | WO2005123873 |
| | | WO2005123873 |
| | | WO2007004380 |
| | | WO2006082742 |
| Osmium(II) complexes | | U.S. Pat. No. 7,279,704 |

TABLE 2-continued

| MATERIAL | EXAMPLES OF MATERIAL | PUBLICATIONS |
|---|---|---|
| | | Organometallics 23, 3745 (2004) |
| Gold complexes | | Appl. Phys. Lett. 74, 1361 (1999) |
| Platinum(II) complexes | | WO2006098120, WO2006103874 |
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE 2-continued

| MATERIAL | EXAMPLES OF MATERIAL | PUBLICATIONS |
| --- | --- | --- |
| 5-member ring electron deficient heterocycles such as triazole, oxadiazole, imidazole, benzoimidazole | | Appl. Phys. Lett. 81, 162 (2002) |
| Triphenylene compounds | | US20050025993 |
| Fluorinated aromatic compounds | | Appl. Phys. Lett. 79, 156 (2001) |

TABLE 2-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |

Electron transporting materials

| | | |
|---|---|---|
| Anthracene-benzoimidazole compounds | | WO2003060956 |
| | | US20090179554 |

TABLE 2-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxy-quinolates (e.g., $Alq_3$, $Zrq_4$) | | Appl. Phys. Lett. 51, 913 (1987)<br>U.S. Pat. No. 7,230,107 |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |

TABLE 2-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 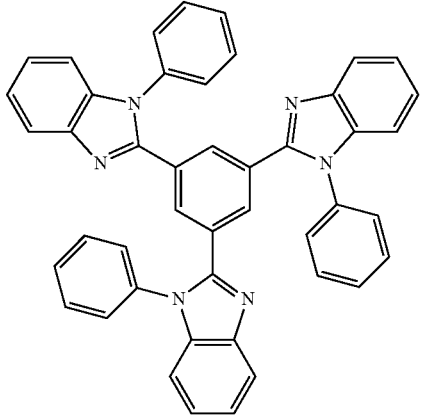 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| | 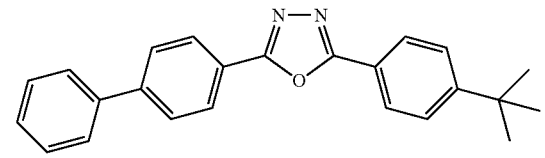 [SMILES: CC(C)(C)c1ccc(-c2nnc(-c3ccc(-c4ccccc4)cc3)o2)cc1] | Appl. Phys. Lett. 55, 1489 (1989) |
| | 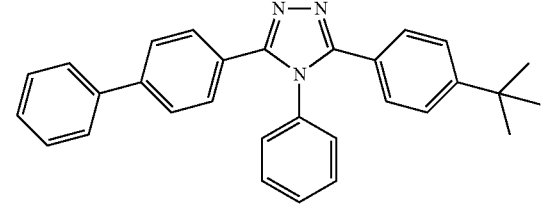 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 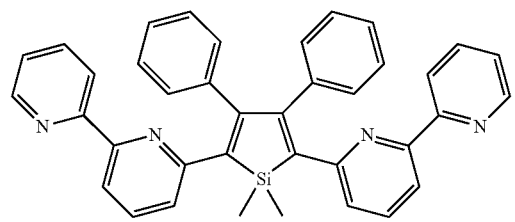 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 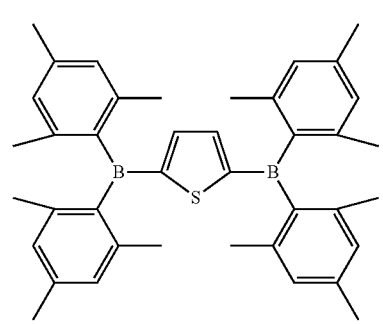 | J. Am. Chem. Soc. 120, 9714 (1998) |
| Fluorinated aromatic compounds | 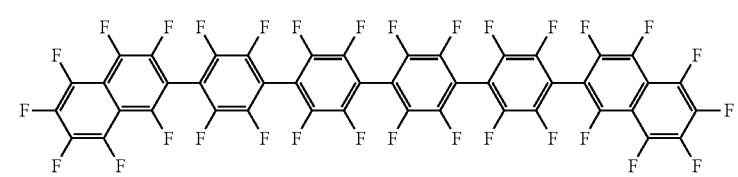 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 2-continued

| MATERIAL | EXAMPLES OF MATERIAL | PUBLICATIONS |
|---|---|---|
| Fullerene (e.g., C60) | | US20090101870 |
| Triazine complexes | | US20040036077 |
| Zn (N^N) complexes | | U.S. Pat. No. 6,528,187 |

EXPERIMENTAL

The intermediates described below were synthesized according to methods reported in *Angewandte. Chem. Int. Ed.* 2010, 49, 4751-4754.

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DCM is dichloromethane, S-Phos is dicyclohexyl (2',6'-dimethoxy-[1,1'-biphenyl]-2-yl)phosphine, Tf is trifluoromethylsulfonate.

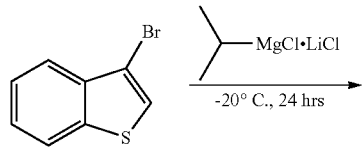

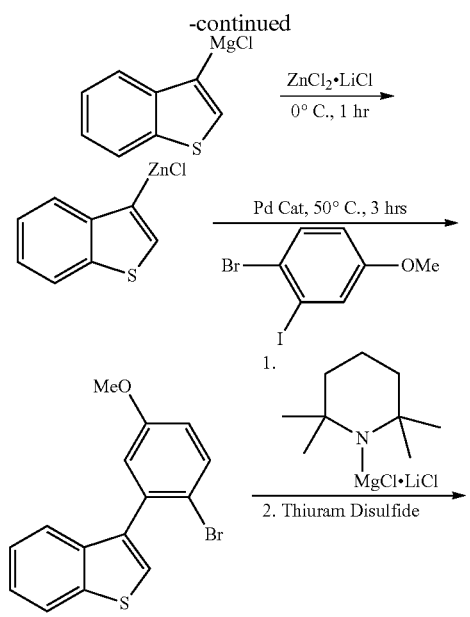

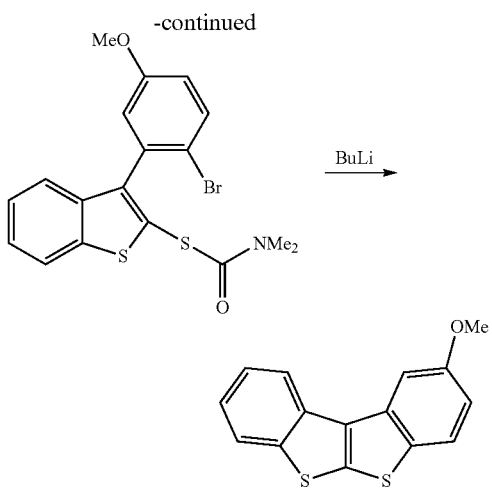

Synthesis of Compound 7

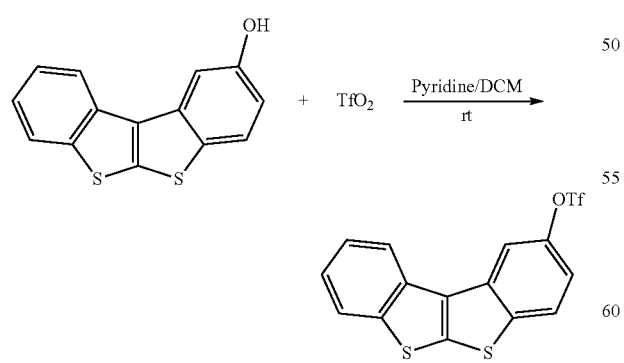

Synthesis of benzo[b]benzo[4,5]thieno[3,2-d]thiophen-2-ol. 2-Methoxy benzo[b]benzo[4,5]thieno[3,2-d]thiophen-2-ol (2.8 g, 10.36 mmol) was dissolved in 100 mL dry DCM and cooled down to −78° C., to which was added 1M BBr₃ DCM solution (15.53 mL), and the reaction was allowed to stir as the reaction was allowed to rise to room temperature. The reaction was monitored by TLC. After workup, 2.5 g (94%) of product was obtained, which was confirmed by NMR.

Synthesis of benzo[b]benzo[4,5]thieno[3,2-d]thiophen-2-yl trifluoromethanesulfonate. Benzo[b]benzo[4,5]thieno[3,2-d]thiophen-2-ol (2.5 g, 9.75 mmol), pyridine (3.09 g, 39 mmol) and 100 mL DCM were charged in a 250 mL flask. To this mixture, TfO₂ (13.76 g, 48.8 mmol) was added slowly and let reaction stirring at room temperature for overnight. After workup, 3 g (80%) of product was obtained, which was confirmed by GC-MS.

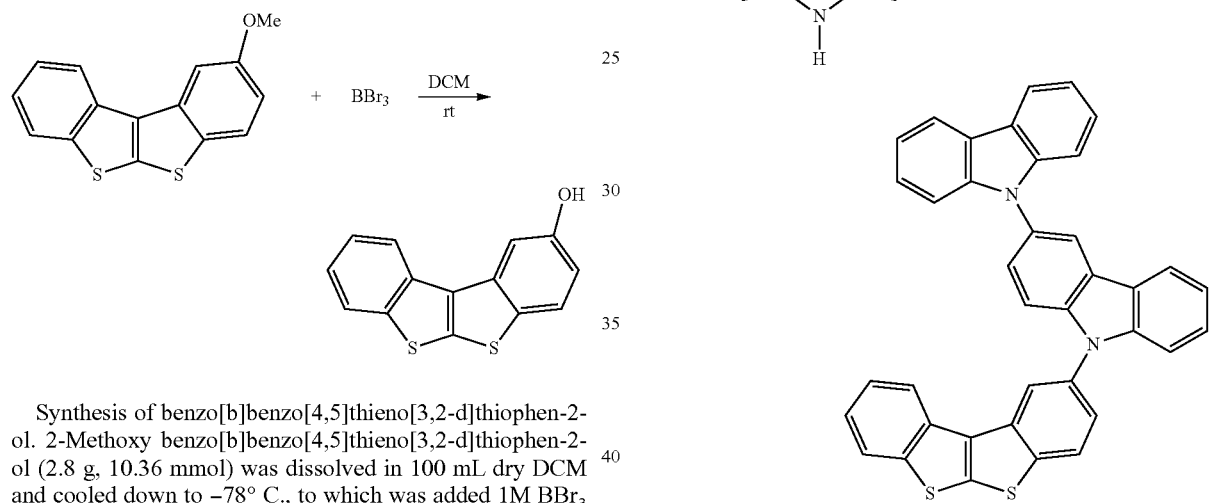

Synthesis of Compound 7

Benzo[b]benzo[4,5]thieno[3,2-d]thiophen-2-yl trifluoromethanesulfonate (1.2 g, 3.09 mmol), Pd2(dba)3 (0.283 g, 0.309 mmol), dicyclohexyl(2',4',6'-triisopropyl-[1,1'-biphenyl]-2-yl)phosphine (0.589 g, 1.236 mmol), 9H-3-Benzo-9'-bicarbazole (1.13 g, 3.4 mmol), sodium tert-butoxide (0.475 g, 4.94 mmol) and 50 mL of m-xylene were charged in a 100 mL flask. The mixture was bubbled with N₂ for 30 minutes then heated to reflux for 3.5 hours. The reaction was cooled down and subjected to aqueous workup. After workup, 1.2 g (68%) white solid product was obtained which was confirmed by NMR.

Synthesis of Compound 3

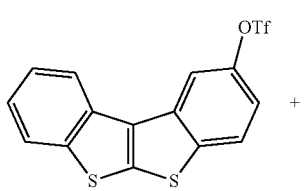

-continued

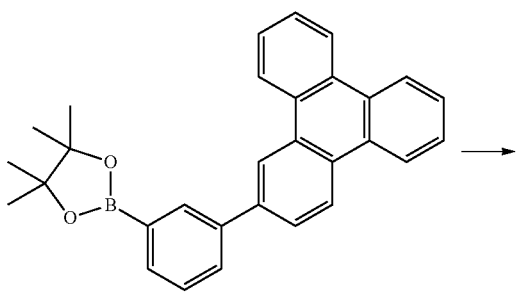

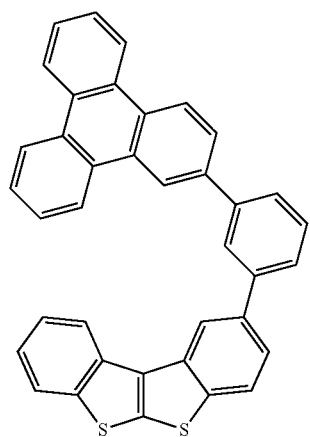

Synthesis of 2-(3-(triphenylen-2-yl)phenyl)benzo[b]benzo[4,5]thieno[3,2-d]thiophene. Benzo[b]benzo[4,5]thieno[3,2-d]thiophen-2-yl trifluoromethanesulfonate (1.5 g, 3.86 mmol), Pd$_2$(dba)$_3$ (0.071 g, 0.077 mmol), dicyclohexyl(2',6'-dimethoxy-[1,1'-biphenyl]-2-yl)phosphine (0.127 g, 0.309 mmol), 4,4,5,5-tetramethyl-2-(3-(triphenylen-2-yl)phenyl)-1,3,2-dioxaborolane (1.82 g, 4.25 mmol), K$_3$PO$_4$ (2.46 g, 11.59 mmol), toluene (90 mL) and water (10 mL) were charged in a 250 mL flask. This mixture was bubbling with nitrogen for 30 minutes then heated up to reflux for overnight. After purification, 1.7 g (81%) of a white solid was obtained. The compound was confirmed by NMR.

Synthesis of Compound 41

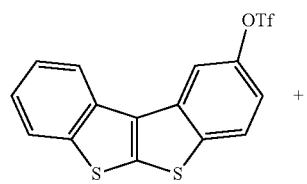

-continued

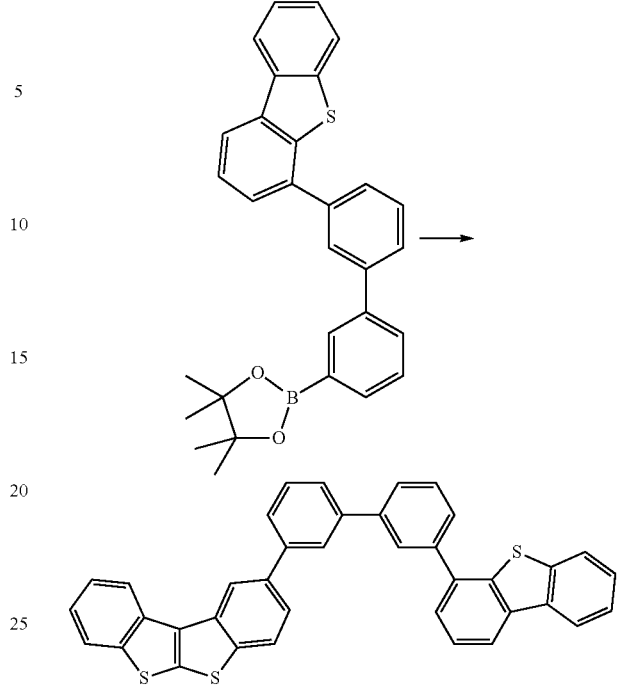

Synthesis of 2-(3'-(dibenzo[b,d]thiophen-4-yl)-[1,1'-biphenyl]-3-yl)benzo[b]benzo[4,5]thieno[3,2-d]thiophene Benzo[b]benzo[4,5]thieno[3,2-d]thiophen-2-yl trifluoromethanesulfonate (1.3 g, 3.35 mmol), Pd$_2$(dba)$_3$ (0.061 g, 0.067 mmol), dicyclohexyl(2',6'-dimethoxy-[1,1'-biphenyl]-2-yl)phosphine (0.11 g, 0.268 mmol), 2-(3'-(dibenzo[b,d]thiophen-4-yl)-[1,1'-biphenyl]-3-yl)-4,4,5,5-tetramethyl-1,3,2-dioxaborolane (1.625 g, 3.51 mmol), K$_3$PO$_4$ (2.13 g, 10.04 mmol), toluene (90 mL) and water (10 mL) were charged in a 250 mL flask. This mixture was bubbled with nitrogen for 30 minutes then heated to reflux overnight. After purification, 1.5 g (78%) of a white solid was obtained. The compound was confirmed by NMR.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

The invention claimed is:
1. A compound having the formula:

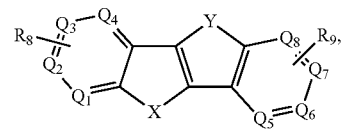

wherein Q$_1$ to Q$_8$ are independently selected from C and N, and wherein Q$_1$ to Q$_8$ may be further substituted;
wherein X and Y are independently selected from the group consisting of O, S, and Se;

wherein R$_8$ and R$_9$ independently represent mono, di, tri, tetra substitution, or no substitution;

wherein R$_8$ and R$_9$ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof;

wherein at least one of R$_8$ and R$_9$ is not hydrogen or deuterium; and wherein at least one of the following is true:

(1) one or more of Q$_1$ to Q$_8$ is N;

(2) Q$_2$ is C substituted by R$_{8\text{-}2}$, which is hydrogen, and Q$_7$ is C substituted by R$_{9\text{-}7}$, which is hydrogen; and (3) each R$_8$ is hydrogen or deuterium.

2. The compound of claim 1, wherein at least one of R$_8$ and R$_9$ is independently selected from the group consisting of:

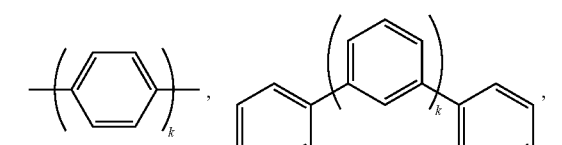

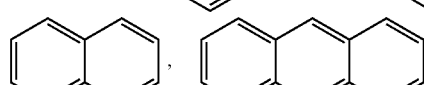

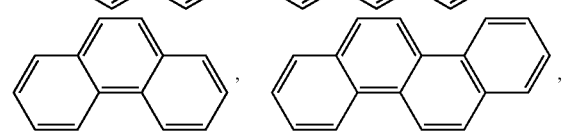

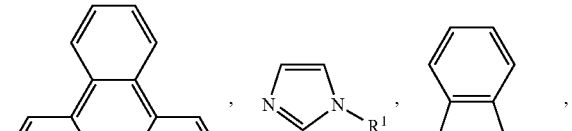

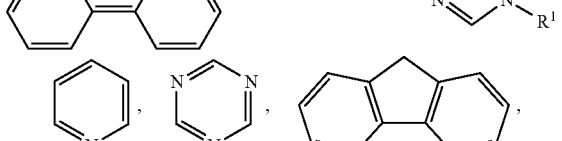

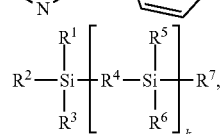

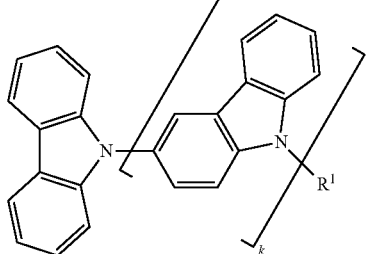

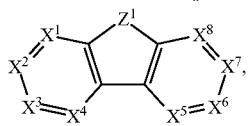

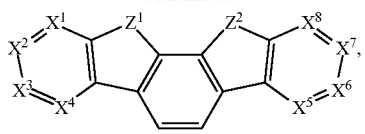

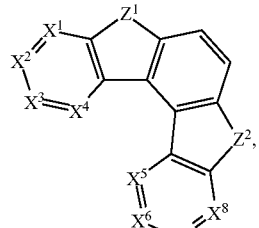

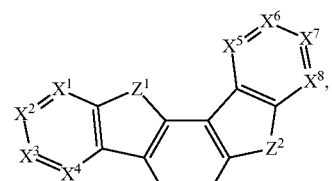

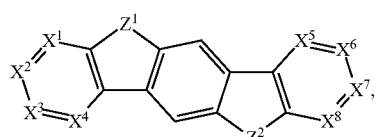

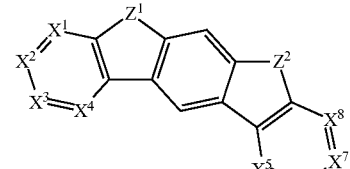

wherein R$^1$ to R$^7$ is independently selected from the group consisting of hydrogen, deuterium, alkyl, cycloalkyl, arylalkyl, alkoxy, aryloxy, amino, silyl, alkenyl, cycloalkenyl, heteroalkenyl, alkynyl, aryl, heteroaryl, and combinations thereof;

wherein k is an integer from 0 to 20;

wherein X$^1$ to X$^8$ are independently selected from C, CH, and N;

wherein Z$^1$ and Z$^2$ is selected from NR$^1$, O, or S; and wherein R$_8$ and R$_9$ may be further substituted.

3. The compound of claim 1, wherein the compound has the formula:

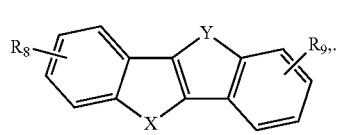

Formula III

4. The compound of claim 1, wherein one of Q$_1$ to Q$_8$ is N.

5. The compound of claim 1, wherein at least one of R$_8$ and R$_9$ has the formula:

Formula IV

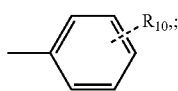

wherein R₁₀ represents mono, di, tri, tetra substitution, or no substitution; and wherein R₁₀ is selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

6. The compound of claim 5, wherein R₁₀ represents mono-substitution and is selected from the group consisting of:

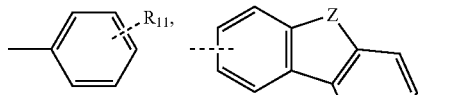

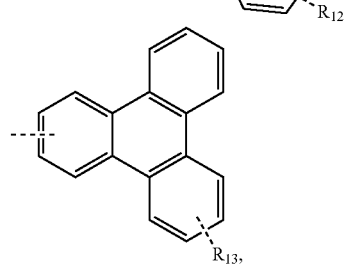

SiRR'R" and combinations thereof;
  wherein Z is selected from the group consisting of NR, S, O, and Se;
  wherein R₁₁, R₁₂, and R₁₃ represents mono, di, tri, tetra substitution, or no substitution; and
  wherein R, R', R", R₁₁, R₁₂, and R₁₃ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

7. The compound of claim 1, wherein at least one of R₈ and R₉ is independently selected from the group consisting of:

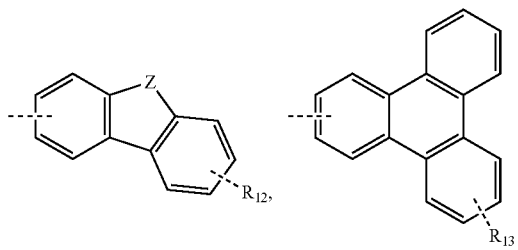

SiRR'R" and combinations thereof;
  wherein Z is selected from the group consisting of NR, S, O, and Se;
  wherein R, R', R", R₁₂, and R₁₃ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof.

8. The compound of claim 1, wherein each R₈ is hydrogen or deuterium.

9. The compound of claim 1, wherein the compound is selected from the group consisting of:

Compound 31

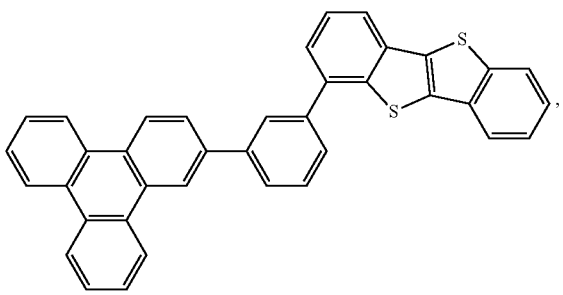

Compound 32

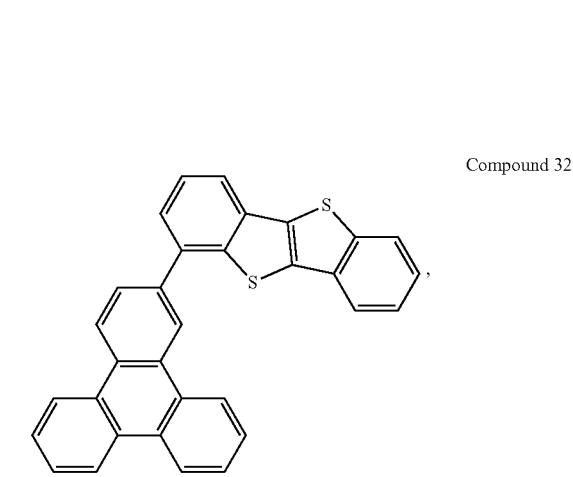

Compound 45

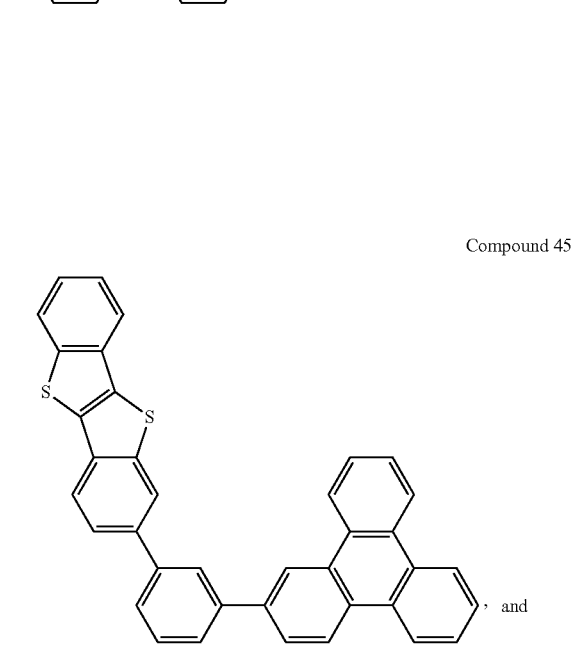

, and

-continued

Compound 46

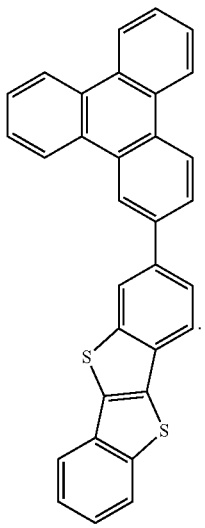

10. A first device comprising an organic light emitting device, further comprising:
   an anode;
   a cathode; and
   an organic layer, disposed between the anode and the cathode, comprising a compound having the formula:

Formula III

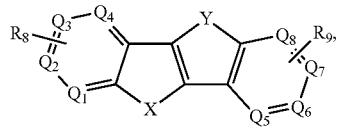

wherein $Q_1$ to $Q_8$ are independently selected from C and N, and wherein $Q_1$ to $Q_8$ may be further substituted;

wherein X and Y are independently selected from the group consisting of O, S, and Se;

wherein $R_8$ and $R_9$ independently represent mono, di, tri, tetra substitution, or no substitution;

wherein $R_8$ and $R_9$ are independently selected from the group consisting of hydrogen, deuterium, alkyl, cycloalkyl, arylalkyl, amino, silyl, germyl, alkenyl, cycloalkenyl, heteroalkenyl, alkynyl, aryl, heteroaryl, and combinations thereof;

wherein at least one of $R_8$ and $R_9$ is not hydrogen or deuterium; and wherein at least one of the following is true:
(1) one or more of $Q_1$ to $Q_8$ is N;
(2) $Q_2$ is C substituted by $R_{8-2}$, which is hydrogen, and $Q_7$ is C substituted by $R_{9-7}$, which is hydrogen; and
(3) each $R_8$ is hydrogen or deuterium.

11. The first device of claim 10, wherein the organic layer is an emissive layer and the compound of Formula III is a host.

12. The first device of claim 10, wherein the organic layer further comprises an emissive dopant.

13. The first device of claim 10, wherein the emissive dopant is a transition metal complex having at least one ligand or part of the ligand if the ligand is more than bidentate selected from the group consisting of:

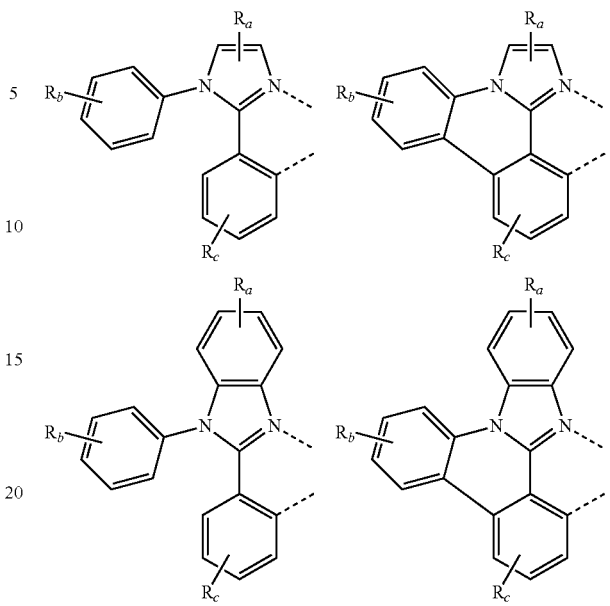

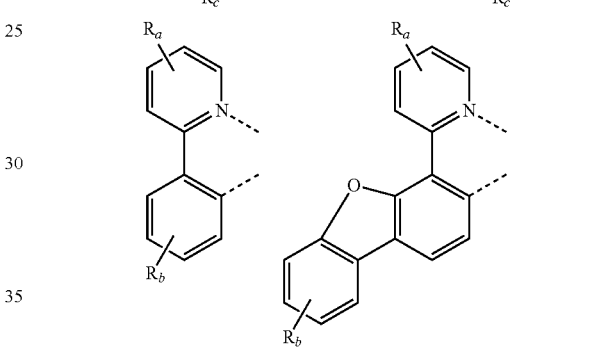

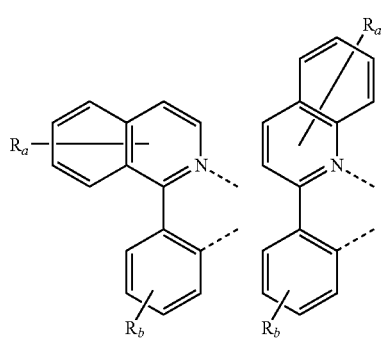

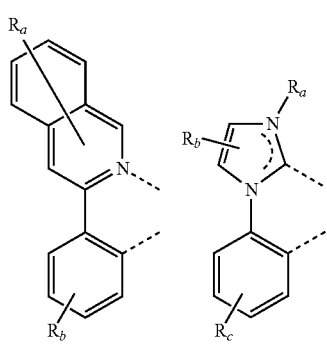

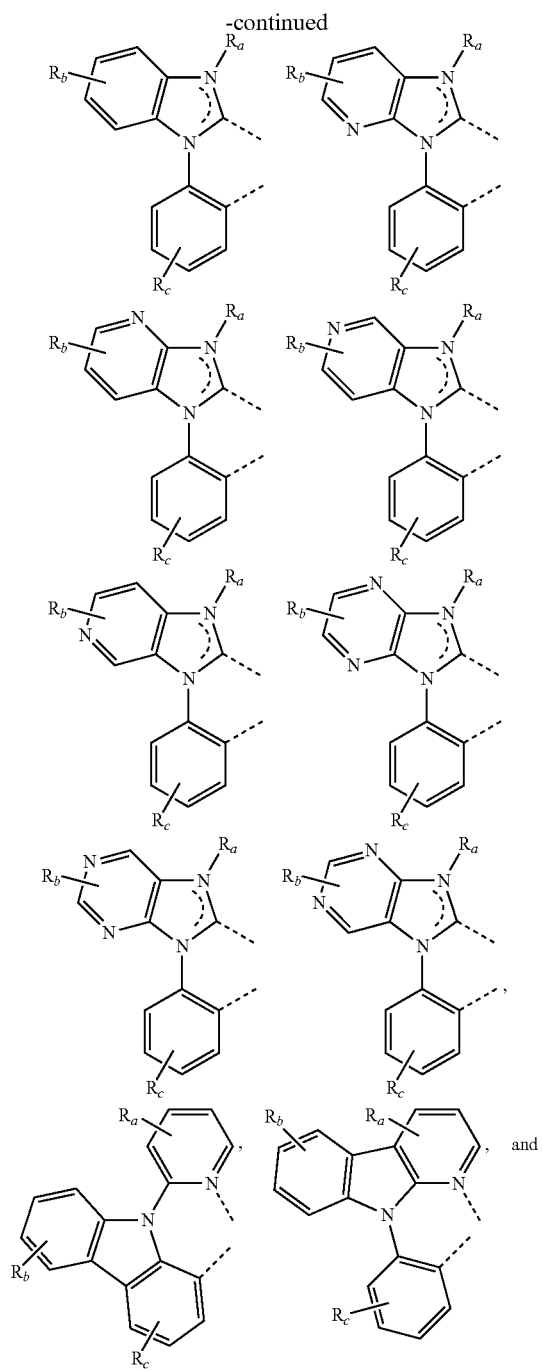

wherein $R_a$, $R_b$, and $R_c$ may represent mono, di, tri, or tetra substitution, or no substitution;

wherein $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, and $R_c$ are optionally joined to form a fused ring or form a multidentate ligand.

14. The first device of claim 10, wherein the device further comprises a second organic layer that is a non-emissive layer and the compound having Formula I is a material in the second organic layer.

15. The first device of claim 14, wherein the second organic layer is a blocking layer and the compound having Formula I is a blocking material in the second organic layer.

16. The first device of claim 10, wherein the first device is a consumer product.

17. The first device of claim 10, wherein the first device is an organic light-emitting device.

18. The first device of claim 10, wherein the first device comprises a lighting panel.

19. The compound of claim 1, wherein $Q_2$ is C substituted by $R_{8\text{-}2}$, which is hydrogen; and $Q_7$ is C substituted by $R_{9\text{-}7}$, which is hydrogen.

20. The compound of claim 1, wherein one or more of $Q_1$ to $Q_8$ is N.

\* \* \* \* \*